United States Patent
Schwarz et al.

(10) Patent No.: US 7,557,136 B2
(45) Date of Patent: Jul. 7, 2009

(54) PYRROLIDINE DERIVATIVES AS OXYTOCIN ANTAGONISTS

(75) Inventors: Matthias Schwarz, Geneve (CH); Catherine Jorand-Lebrun, Contamine-Sarzin (FR); Delphine Valognes, Asson (FR)

(73) Assignee: Laboratoires Serono SA, Coinsins (CH)

( * ) Notice: Subject to any disclaimer, the term of this patent is extended or adjusted under 35 U.S.C. 154(b) by 308 days.

(21) Appl. No.: 10/547,032

(22) PCT Filed: Feb. 16, 2004

(86) PCT No.: PCT/EP2004/050142

§ 371 (c)(1),
(2), (4) Date: Sep. 27, 2006

(87) PCT Pub. No.: WO2004/076407

PCT Pub. Date: Sep. 10, 2004

(65) Prior Publication Data

US 2007/0037806 A1 Feb. 15, 2007

(30) Foreign Application Priority Data

Feb. 27, 2003 (EP) ................... 03100477

(51) Int. Cl.
| A61K 31/40 | (2006.01) |
| A61K 31/4245 | (2006.01) |
| A61K 31/4184 | (2006.01) |
| C07D 207/14 | (2006.01) |
| C07D 271/06 | (2006.01) |
| C07D 403/06 | (2006.01) |

(52) U.S. Cl. .................. 514/423; 514/364; 514/385; 548/539; 548/131; 548/306.1

(58) Field of Classification Search .......... 548/131, 548/306.1, 539; 514/364, 385, 423
See application file for complete search history.

(56) References Cited

U.S. PATENT DOCUMENTS

| 2003/0212012 A1 | 11/2003 | Halazy et al. |
| 2004/0147511 A1 | 7/2004 | Schwarz et al. |
| 2004/0220238 A1 | 11/2004 | Schwarz et al. |

FOREIGN PATENT DOCUMENTS

| WO | 01/72705 | 10/2001 |
| WO | 02/074741 | 9/2002 |
| WO | 02/102799 | 12/2002 |

OTHER PUBLICATIONS

Martius et al. European Journal of Obstetrics & Gynecology and Reproductive Biology 1998, 80, 183-189.*

Papatsonis et al. Evidence-Based Medicine 2006, 11, 75.*

Gimpl Gerald, Fahrenholz Falk: "The Oxytocin Receptor System: Structure, Function, and Regulation", Physiological Reviews, vol. 81, No. 2, pp. 629-683, Apr. 2001.

Maggi, Mario et al.: "Human Myometrium during Pregnancy Contains and Responds to V1 Vasopressin Receptors as well as Oxytocin Receptors", Journal of Clinical Endocrinology and Metabolism, vol. 70, No. 4, pp. 1142-1154, 1990.

Mitchell B.F., Schmid Birgit: "Oxytocin and its Receptor in the Process of Parturition", J. Soc. Gynecol. Investig., vol. 8, No. 3, pp. 122-133, May/Jun. 2001.

Thornton, Steven et al.: "Oxytocin antagonist: clinical and scientific considerations", Experimental Physiology, vol. 86, No. 2, pp. 297-302, 2001.

Evans, Ben E. et al.: "Orally Active, Nonpeptide Oxytocin Antagonists", J. Med. Chem., vol. 35, pp. 3919-3927, 1992.

Cook, Neil et al.: "SPA: a revolutionary new technique for drug screenings", Pharmaceutical Manufacturing International, pp. 49-53, 1992.

U.S. Appl. No. 11/449,802, filed Jun. 9, 2006, Schwarz, et al.

* cited by examiner

*Primary Examiner*—Rebecca L Anderson
*Assistant Examiner*—Jason Nolan
(74) *Attorney, Agent, or Firm*—Oblon, Spivak, McClelland, Maier & Neustadt, P.C.

(57) ABSTRACT

The present invention relates to novel pyrrolidine derivatives of Formula (I), its geometrical isomers, its optically active forms as enantiomers, diastercomers, mixtures of these and its racemate forms, as well as salts thereof, wherein: $R^1$'s selected from the group comprising or consisting of H and $C_1$-$C_6$-alkyl; $R^2$ is selected from the group comprising or consisting of hydrogen, $C_1$-$C_6$-alkyl, $C_1$-$C_6$ alkyl aryl, heteroaryl, $C_1$-$C_6$ alkyl heteroaryl, $C_2$-$C_6$-alkenyl, $C_2$-$C_6$-alkenyl aryl, $C_2$-$C_6$ alkenyl heteroaryl, $C_2$-$C_6$-alkynyl, $C_2$-$C_6$-alkynyl aryl, $C_2$C_6$-alkynyl heteroaryl, $C_3$-$C_8$ cycloalkyl, heterocycloalkyl, CI-C6-alkyl cycloallcyl, CI-C6-alkyl heterocycloalkyl, CIC6 alkyl carboxy, acyl, $C_1$-$C_6$-alkyl acyl, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, $C_1$-$C_6$-alkyl acylarnino, $C_1$-$C_6$-alkyl ureido, amino, $C_1$-$C_6$-alkyl amino, sulfonyloxy, $C_1$-$C_6$ alkyl sulfonyloxy, sulfonyl, $C_1$-$C_6$-alkyl sulfonyl, sulfinyl, $C_1$-$C_6$-alkyl sulfinyl, $C_1$-$C_6$alkyl sulfanyl, $C_1$-$C_6$-alkyl sulfonylamino.

(I)

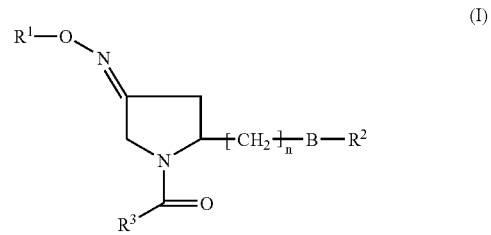

15 Claims, No Drawings

PYRROLIDINE DERIVATIVES AS OXYTOCIN ANTAGONISTS

FIELD OF THE INVENTION

The present invention relates to novel pyrrolidine derivatives, in particular for use as medicaments, as well as pharmaceutical formulations containing such pyrrolidine derivatives. Said pyrrolidine derivatives are useful in the treatment and/or prevention of preterm labor, premature birth, and dysmenorrhea Preferably, the pyrrolidine derivatives display a modulatory, notably an antagonist activity of the oxytocin receptor. More preferably, said compounds are useful in the treatment and/or prevention of disease states mediated by oxytocin, including preterm labor, premature birth and dysmenorrhea.

BACKGROUND OF THE INVENTION

In the field of obstetrics, one of the most important problems is the management of preterm labor and premature birth as they represent a major cause of perinatal morbidity and mortality.

For the treatment of preterm labor the use of magnesium sulfate and ethanol has been suggested. However, magnesium sulfate at plasma concentrations above the therapeutic range of 4 to 8 mg/dL can cause inhibition of cardiac conduction and neuromuscular transmission, respiratory depression and cardiac arrest, thus making this agent unsuitable notably when the renal function is impaired.

Ethanol is effective in preventing premature labor, but it does not produce a corresponding reduction in the incidence of fetal respiratory distress. Also, ethanol is assumed to have a negative impact on the fetus.

Two further therapeutic agents fall into either of the groups of:
  a) β2-adrenergic agonists, or
  b) oxytocin antagonists.

The β2-adrenergic receptor generally causes an inhibitory action within the cells wherein it is expressed (muscles, heart, uterus etc). β2-adrenergic agonists are used to activate said inhibitory action of the receptor. Hence, β2-adrenergic agonists are sympathomimetics which—among others—inhibit uterine contractility. Known β2-adrenergic agonists for the treatment of preterm labor are Ritodrine, Tetbutaline and Albuterol.

Ritodrine (i.e. (R*,S*)-4-Hydroxy-.alpha.-[1-[[2-(4-hydroxyphenyl)ethyl]amino]ethyl]-benzenemethanol; see U.S. Pat. No. 3,410,944 of N. V. Philips) is the leading $β_2$-adrenergic agonist but causes a number of cardiovascular and metabolic side effects in the mother, including tachycardia, increased renin secretion, hyperglycemia (and reactive hypoglycemia in the infant).

Terbutaline (i.e. 5-[2-[(1,1-Dimethylethyl)amino]-1-hydroxyethyl]-1,3-benzenediol, see U.S. Pat. No. 3,937,838, Draco) and Albuterol ($α^1$-[[(1,1-Dimethylethyl)amino]methyl]-4-hydroxy-1,3-benzenedimethanol; U.S. Pat. No. 3,644,353, Allen and Hanburys) are further $β_2$ -adrenergic agonists and have side effects similar to those of Ritodrine.

A more recent approach of treating preterm labor consists in the use of oxytocin antagonists.

Oxytocin (OT) is a cyclic nona-peptide whose actions are mediated by activation of specific G protein-coupled receptors currently classified into OT receptors (OT-R) (1).

Oxytocin (OT) causes the contraction of the uterus of mammals during labor. The corresponding oxytocin receptor belongs to the family of G-protein-coupled receptors and is similar to $V_1$ and $V_2$ vasopressin receptors. OT receptors increase dramatically during the course of pregnancy. The concentration of OT receptors has been shown to correlate with spontaneous uterine activity (2-3). OT-induced contractions of the uterus during labor result in the dilatation of the cervix and eventually in the movement of the foetus through the vaginal canal. In some cases, these contractions occur before the foetus is fully viable, resulting in premature labor. Premature labor and premature birth are undesired as they are major causes of perinatal morbidity. Hence, the management of preterm labor represents a significant problem in the field of obstetrics.

In recent years, strong evidence has accumulated indicating that the hormone oxytocin plays a major role in initiating labor in mammals, in particular in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process. This "up-regulation" of oxytocin receptors and increased uterine sensitivity seems to be due to trophic effects of rising plasma levels of estrogen towards term. By down-regulating oxytocin, it is expected that both the direct (contractile) and indirect (increased prostaglandin synthesis) effects of oxytocin on the uterus could be blocked. An oxytocin modulator, e.g. blocker or antagonist would likely be efficacious for treating preterm labor.

A further condition related to oxytocin is dysmenorrhea, which is characterised by pain or discomfort associated with menses. The pain is believed to result from uterine contractions and ischemia, probably mediated by the effect of prostaglandins produced in the secretory endometrium. By blocking both the indirect and direct effects of oxytocin on the uterus, an oxytocin antagonist would be a likely candidate for treating dysmenorrhea Some agents counteracting the action of oxytocin are currently used in clinical studies (4).

Atosiban, a peptide OT antagonist which is already on the market, suffers the problem of most peptides: low oral bio-avail-ability resulting from intestinal degradation. Such compounds must be administered parenterally.

The development of non-peptide ligands for peptide hormone receptors is expected to overcome this problem. Small molecule selective oxytocin antagonists have been reported by Merck. In addition to cyclic hexapeptides, Merck suggested indanylpiperidines and tolyl-piperazines as orally deliverable OT antagonists (5). In WO 96/22775 and U.S. Pat. No. 5,756,497, Merck reported benzoxazinylpiperidines or benzoxainones as OT receptor antagonists.

Specific sulfonamides have been reported to antagonize ocytocin at the ocytocin receptor. Elf Sanofi's EP-A-0469984 and EP-A-0526348 report N-sulfonyl indolines acting as antagonists of the vasopressin and the oxytocin receptors.

American Cyanamid's U.S. Pat. No. 5,889,001 claims pyrazole benzodiazepine derivatives as vasopressin and oxytocin antagonists.

The OT antagonists disclosed in WO 01/72705, WO 02/074741 and WO 02/102799 (Applied Research Systems ARS Holding) arc pyrrolidine-typo compounds.

SUMMARY OF THE INVENTION

In a first aspect, the invention provides novel pyrrolidine derivatives of formula I:

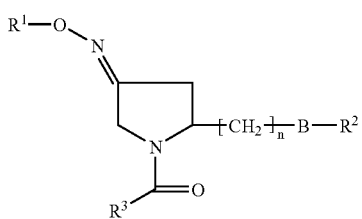

In a second aspect, the present invention provides novel pyrrolidine derivatives of formula (I) for use as a medicament.

In a third aspect, the invention provides a compound of formula I, for the preparation of a pharmaceutical composition useful in the treatment and/or prevention of preterm labor, premature birth, dysmenorrhea In a fourth aspect invention provides a method of synthesis of a compound according to formula I.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4oxadiazolyl, 1,2,5-oxadiazolyl, 1,3,4-oxadiazolyl, 1,3,4-triazinyl, 1,2,3-triazinyl, benzofuryl, [2,3-dihydro]benzofuranyl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$-$C_6$-alkyl cycloalkyl" refers to $C_1$-$C_6$-alcyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_5$-alkyl groups having an carboxy substituent, including 2-carboxyethyl and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"$C_1$-$C_6$-alkyl acyl" refers to $C_1$-$C_6$-alkyl groups having an acyl substituent, including 2-acetylethyl and the like.

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"$C_1$-$C_6$-alkyl alkoxy" refers to $C_1$-$C_5$-alkyl groups having an alkoxy substituent, including 2-ethoxyethyl and the like.

"Alkoxycarbonyl" refers to the group —C(O)OR where R includes H, "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen or "$C_1$-$C_6$-alkyl" or "aryl" or "heteroaryl" or "$C_1$-$C_6$alkyl aryl" or "$C_1$-$C_6$-alkyl heteroaryl".

"$C_1$-$C_6$-alkyl acylamino" refers to $C_1$-$C_6$-alkyl groups having an acylamino substituent, including 2-(propionylamino) ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl","heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$alkenyl heteroaryl", "$C_2$-$C_6$-alkynyl aryl", "$C_2$-$C_6$-alkynylheteroaryl", "$C_1$-$C_6$ alkyl cycloalkyl", "$C_1$-$C_6$-alkyl heterocycloalkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_5$-alkyl groups having an amino substituent including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "aryl", "heteroaryl", "$C_1$-$C_6$-alkyl aryl" or "$C_1$-$C_6$-alkyl heteroaryl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_1$-$C_6$-alkyl aryl" or "$C_1$-$C_6$-alkyl heteroaryl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "aryl", "heteroaryl", "$C_1$-$C_6$-alkyl aryl" or "$C_1$-$C_6$-alkyl heteroaryl".

"$C_1$-$C_6$-alkyl sulfinyl" refers to $C_1$-$C_6$-alkyl groups having a sulfinyl substituent including 2-(methylsulfinyl)ethyl and the like.

"Sulfanyl" refers to groups —S—R where R includes "$C_1$-$C_6$-alkyl" or "aryl" or "hetero-aryl" or "$C_1$-$C_6$-alkyl aryl" or "$C_1$-$C_6$-alkyl heteroaryl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' is independently hydrogen or "$C_1$-$C_6$-alkyl" or "aryl" or "heteroaxyl" or "$C_1$-$C_6$-alkyl aryl" or "$C_1$-$C_6$-alkyl heteroaryl".

"$C_1$-$C_6$-alkyl sulfonylamino" refers to $C_1$-$C_6$-alkyl groups having a sulfonylamino substituent, including 2-ethylsulfonylamino)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate," "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refer to salts or complexes of the below-specified compounds of formula (I). Examples of such salts include, but are not restricted, to base addition salts formed by reaction of compounds of formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperaxine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have an activity as OT-R antagonists.

The term "preterm labor" or the term "premature labor" shall mean expulsion from the uterus of an infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "caesarean delivery" shall mean incision through the abdominal and uterine walls for delivery of a foetus.

The compounds according to the present invention are those of formula I

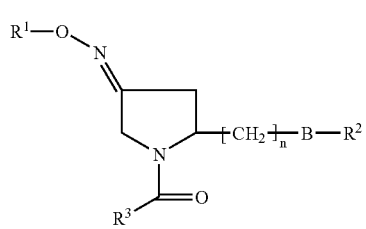

The present invention also includes the geometrical isomers, the optical active forms, enantiomers, diastereomers of compounds according to formula (I), mixtures of these, as well as their racemates and also pharmaceutically acceptable salts.

$R^1$ in formula (I) is selected from the group comprising or consisting of H and substituted or unsubstituted $C_1$-$C_6$-alkyl. Preferably $R^1$ is H or methyl.

B in formula (I) is selected from the group consisting of —COO, —CONR$^4$, oxadiazole, thiadiazole or benzimidazole.

Thereby, $R^4$ is selected from the group comprising or consisting of H or substituted or unsubstituted $C_1$-$C_6$-alkyl. Preferably, $R^4$ is H or $C_1$-$C_3$-alkyl, like a methyl or ethyl group.

$R^2$ in formula (I) is selected from the group comprising or consisting of hydrogen, substituted or unsubstituted $C_1$-$C_6$-alkyl, substituted or unsubstituted aryl, substituted or unsubstituted $C_1$-$C_6$-alkyl aryl, substituted or unsubstituted heteroaryl, substituted or unsubstituted $C_1$-$C_6$-alkyl heteroaryl, substituted or unsubstituted $C_2$-$C_6$alkenyl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl, substituted or unsubstituted $C_2$-$C_6$-alkynyl aryl, substituted or unsubstituted $C_2$-$C_6$-alkynyl heteroaryl, substituted or unsubstituted $C_3$-$C_8$-cycloalkyl, substituted or unsubstituted heterocycloalkyl, substituted or unsubstituted $C_1$-$C_6$-alkyl cycloalkyl, substituted or unsubstituted $C_1$-$C_6$-alkyl heterocycloalkyl, substituted or unsubstituted $C_1$-$C_6$-alkyl carboxy, acyl, substituted or unsubstituted $C_1$-$C_6$-alkyl acyl, substituted or unsubstituted $C_1$-$C_6$-alkyl acyloxy, substituted or unsubstituted $C_1$-$C_6$-alkyl alkoxy, alkoxycarbonyl, substituted or unsubstituted $C_1$-$C_6$-alkyl alkoxycarbonyl, aminocarbonyl, substituted or unsubstituted $C_1$-$C_6$-alkyl aminocarbonyl, substituted or unsubstituted $C_1$-$C_6$-alkyl acylamino, substituted or unsubstituted $C_1$-$C_6$-alkyl ureido, substituted or unsubstituted $C_1$-$C_6$-alkyl amino, substituted or unsubstituted $C_1$-$C_6$-alkyl sulfonyloxy, sulfonyl, substituted or unsubstituted $C_1$-$C_6$-alkyl sulfonyl, sulfinyl, substituted or unsubstituted $C_1$-$C_6$-alkyl sulfinyl, substituted or unsubstituted $C_1$-$C_6$-alkyl sulfanyl, substituted or unsubstituted $C_1$-$C_6$-alkyl sulfonylamino.

$R^3$ in formula (I) is selected from the group comprising or consisting of substituted or unsubstituted aryl and substituted or unsubstituted heteroaryl.

Alternatively, $R^2$ and $R^4$ in formula (I) may form—together with the N atom to which they are linked—a substituted or unsubstituted, 5-8 membered saturated or unsaturated heterocycloalkyl ring, e.g. a piperidinyl, piperazinyl or morpholino moiety. Such ring may be optionally fused with an aryl, heteroaryl, cycloalkyl or heterocycloalkyl ring.

n in formula (I) is an integer from 1 to 3. More preferred is 1 or 2.

According to one embodiment, $R^3$ in compounds of formula (I) is an unsubstituted or substituted aryl group (e.g. a phenyl). An example of a substituted aryl group is a biphenyl or 2-methyl biphenyl moiety.

According to a further embodiment B is either an ester —COO, an amide CONR$^4$ or an oxadiazole.

According to still a further embodiment $R^2$ is selected from the group consisting of H, substituted or unsubstituted $C_1$-$C_6$ alkyl, 3-8 membered cycloalkyl or $R^2$ undergoes a ring closure with $R^4$ to form a substituted or unsubstituted morpholino moiety.

According to still a further embodiment the pyrrolidine derivative according to formula (I) are those wherein $R^1$ is methyl, $R^3$ is a biphenyl moiety, B is—COO, CONR$^4$ or a 1,2,4 oxadiazole moiety.

Compounds of formula (I) may be used as a medicament.

Specifically, the compounds of formula (I) are suitable for use in treating disorders such as preterm labor, premature birth, dysmenorrhea and for stopping labor prior to cesarean delivery. The compounds of the present invention are in particular useful for the treatment of preterm labor, premature birth and dysmenorrhea Preferably, the compounds according to formula (I) alone or in a form of a pharmaceutical composition are suitable for the modulation of oxytocin function(s), thus specifically allowing the treatment and/or prevention of disorders that are mediated by the oxytocin receptor. Such modulation preferably involves the inhibition of OT-R function(s), notably by the antagonization of the oxytocin receptor in mammals, and in particular in humans.

Abnormal activity or hyperactivity of the oxytocin receptor are frequently involved in various disorders including the above enumerated disorders and disease states. Hence, the compounds according to the invention may be used for the treatment of disorders by modulating OT-R function or pathways. The modulation of the OT-R function or pathways may involve the down-regulation and/or inhibition of the oxytocin receptor. The compounds of the invention may be employed alone or in combination with further pharmaceutical agents, e.g. with a further OT-R modulator.

When employed as pharmaceuticals, the pyrrolidine derivatives of the present invention are typically administered in the form of a pharmaceutical composition. Hence, pharmaceutical compositions comprising a compound of Formula (I) and a pharmaceutically acceptable carrier, diluent or excipient are also within the scope of the present invention. A person skilled in the art is aware of a whole variety of such carriers, diluents or excipients suitable to formulate a pharmaceutical composition.

The compounds of the invention, together with a conventionally employed adjuvant, carrier, diluent or excipient may be formulated as pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the pyrrolidine derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention may be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrrolidine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-bufferd saline or other injectable carriers known in the art. As above mentioned, the pyrrolidine derivatives of Formula (I) in such compositions is typically a minor component, frequently ranging between 0.05 to 10% by weight with the remainder being the injectable carrier and the like.

The above-described components for orally administered or injectable compositions are merely representative. Further materials as well as processing techniques and the like are set out in Part 8 of (6).

The compounds of this invention can also be administered in sustained release forms or from sustained release drug delivery systems. A description of representative sustained release materials can also be found in (6).

Still a further object of the present invention is a process for preparing pyrrolidine derivatives according to formula I.

a) Preparation of Ester Pyrrolidines

According to one process, pyrrolidine derivatives Ia according to the general formula (I), whereby the substituent B is an ester, are prepared from the corresponding carboxylic acid compounds II and alcohol III, whereby the substituents $R^1$-$R^3$ and n are as above defined, using standard synthetic techniques as hereinafter described in the Examples and shown in Scheme 1.

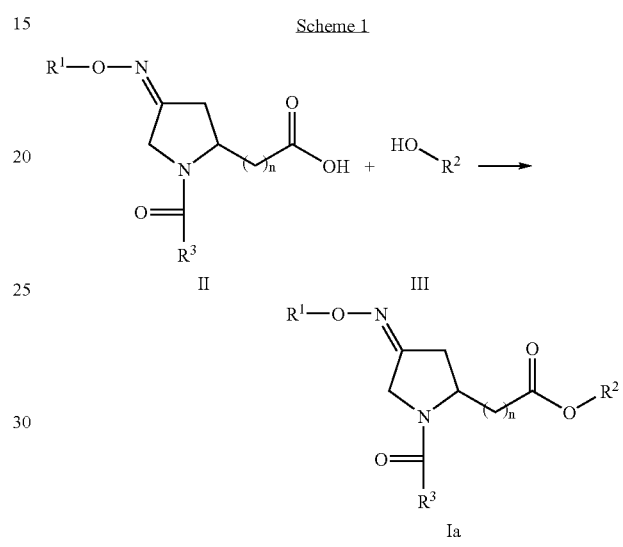

The pyrrolidine-2-carboxylic acids II, whereby the substituents $R^1$, $R^3$ and n are as above defined, are prepared from the corresponding ketone IV and substituted hydroxylamines V, whereby the substituents $R^1$, $R^3$ and n are as above defined, using standard synthetic techniques as hereinafter described in the Examples and shown in Scheme 2.

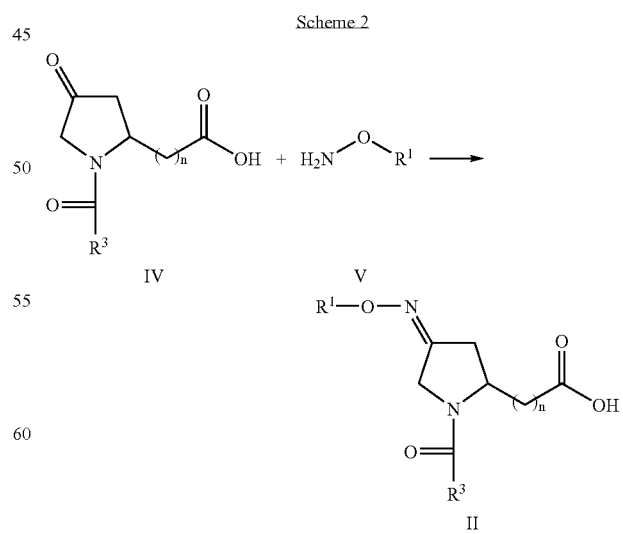

Compounds of formula V are obtained from commercial sources or prepared from N-Boc-hydroxylamine VI and alkylating agents VII (X=Cl, Br, I), by standard synthetic techniques, as shown in Scheme 3.

Scheme 3

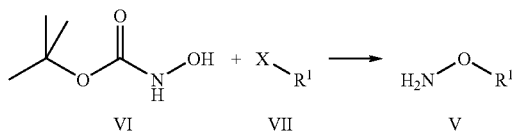

The keto compounds of general formula IV, whereby the substituents R³ and n are as above defined, may be prepared by oxidation of alcohol compounds of general formula VIII, whereby the substituents R³ and n are as above defined, as hereinafter described in the Examples and shown in Scheme 4.

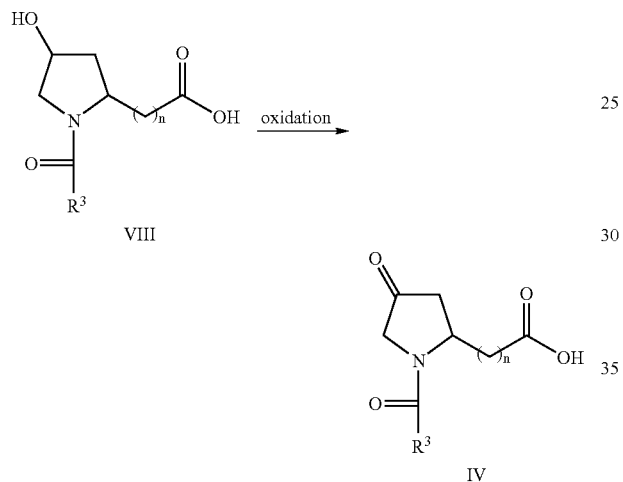

The alcohol compounds of general formula VIII, whereby the substituents R³ and n are as above defined, can be prepared by reaction of a compound of general formula IX whereby n is as above defined, with an acylating agent X of general formula R³—CO—Y—whereby R³ is as defined above defined and Y is any appropriate leaving group (e.g. Cl, OH)—as illustrated in Scheme 5.

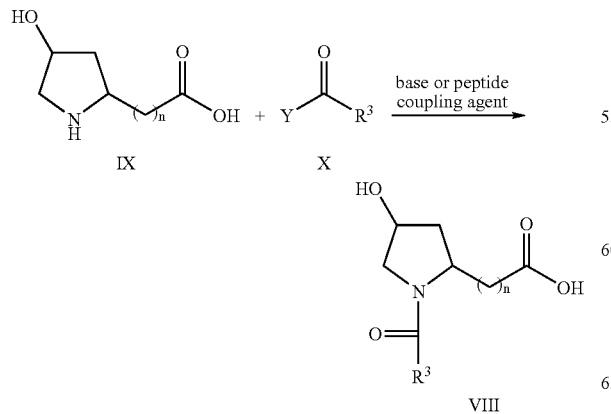

The acid compounds of general formula IX, whereby n is 1 is the commercially available (4hydroxypyrrolidin-2-yl, IXa), and whereby n is 2 can be prepared by oxidation of commercially available, 4-hydroxyproline XI, using standard synthetic techniques as hereinafter described in the Examples and shown in Scheme 6.

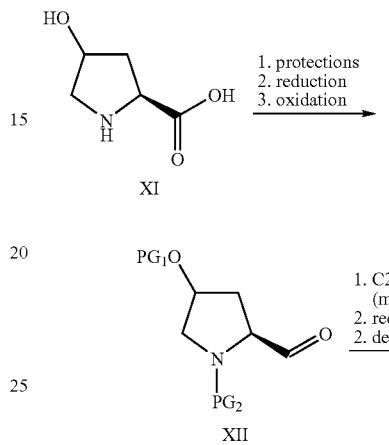

According to one process, pyrrolidine derivatives according to the general formula (I), whereby the substituent B is an ester and R² is methyl can be prepared either from the corresponding carboxylic acid compounds II or in few steps from the alcohol VIII, as hereinafter described in the Examples and shown in Scheme 7.

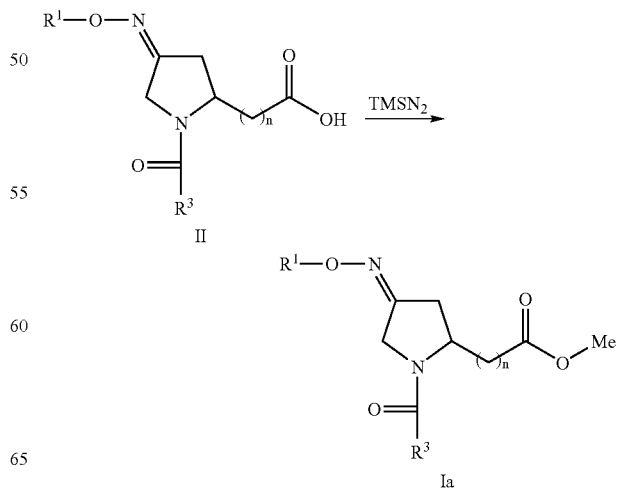

-continued

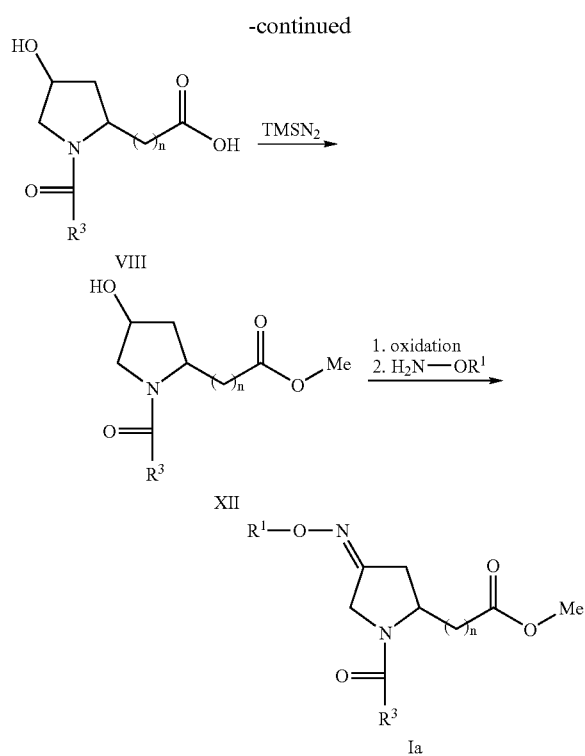

b) Preparation of Amide Pyrrolidines

According to one process, pyrrolidine derivatives Ib according to the general formula (I), whereby the substituent B is an amide, are prepared from the corresponding carboxylic acid compounds II and amine XIII, whereby the substituents $R^1$-$R^3$ and n are as above defined, using standard synthetic techniques as hereinafter described in the Examples and shown in Scheme 8.

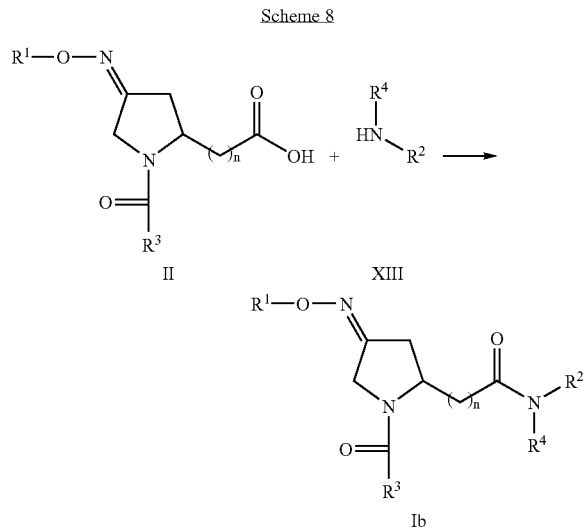

c) Preparation of Oxadiazole Pyrrolidines

According to one synthetic approach, pyrrolidine derivatives Ic according to the general formula (I), whereby the substituent B is a 1,2,4 oxadiazole of formula, may be prepared from the corresponding carboxylic acid compounds II and amidoximes XIV, whereby the substituents $R^1$-$R^3$ are as above defined, by well known solutionphase chemistry protocols, such as those described in the Examples and shown in Scheme 9.

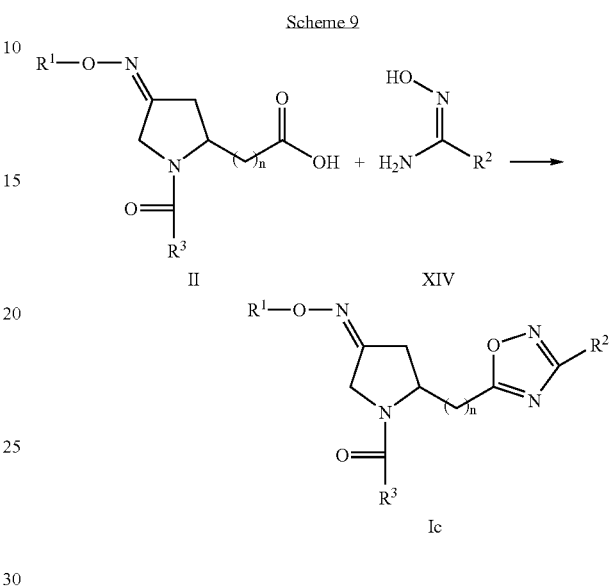

The amidoxime components XIV whereby the substituent $R^2$ is as above defined, are either obtained from commercial sources or made from the corresponding nitrites XV, by treatment of the latter with hydroxylamine under standard conditions well known to the person skilled in the art, such as those described in the Examples and shown in Scheme 10.

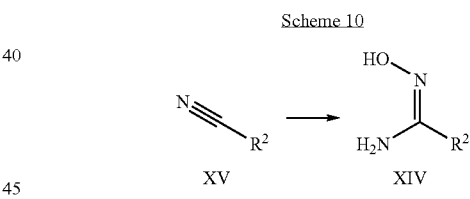

The nitrile components XV are either obtained from commercial sources or made from, e.g. the corresponding carboxylic acids XVI, as shown in Scheme 11, by any of the functional group inter-conversion methods well known to the person skilled in the art, used to transform a carboxylic acid into the corresponding nitrile.

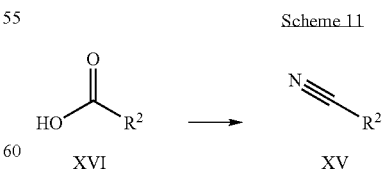

According to a further synthetic approach, pyrrolidine derivatives Id according to the general formula (I), whereby the substituent B is a 1,2,4 oxadiazole, may be prepared from the corresponding amidoxime compounds XVII and acids XVI, whereby the substituents $R^1$-$R^3$ are as above defined, by well known solution-phase chemistry protocols, such as those described in the Examples and shown in Scheme 12.

d) Preparation of Benzimidazole Pyrrolidines

According to one synthetic approach, pyrrolidine derivatives Ie according to the general formula (I), whereby the substituent B is a benzimidazole, may be prepared by cyclisation of the corres-ponding anilide compounds Ib, whereby the substituents $R^1$-$R^3$ are as above defined, such as those described in the Examples and shown in Scheme 14.

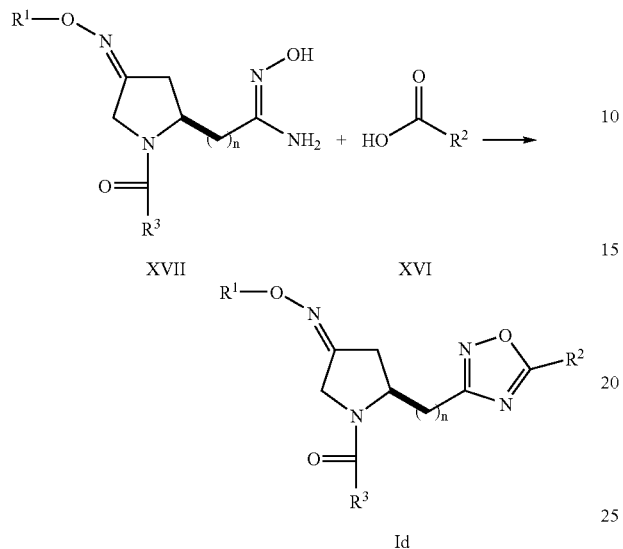

The amidoxime components XVI whereby the substituent $R^1$, $R^3$ and n are as above defined, are obtained from the corresponding acid II in two steps under standard conditions well known to the person skilled in the art shown in Scheme 13.

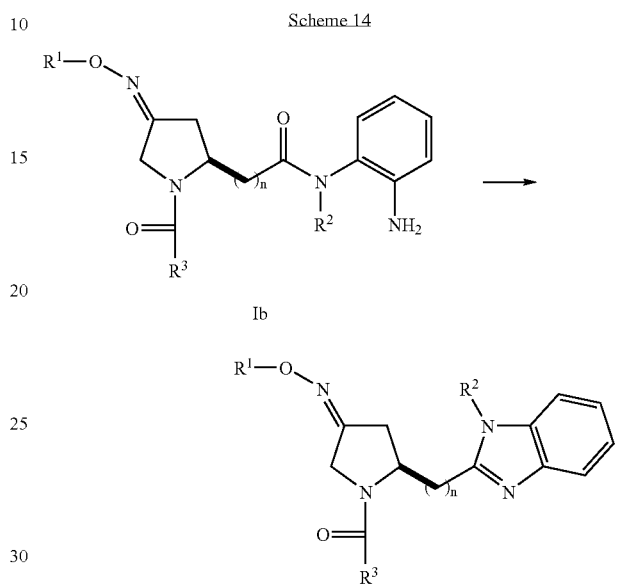

e) Preparation of Modified Compounds and Purification

According to a further general process, compounds of formula (I) may be converted to alternative compounds of formula I', whereby the substituent $R^{2'}$ is defined as $R^2$, by suitable protection/deprotection/functional group interconversion techniques of substituent $R^2$ well known to the person skilled in the ark as shown in Scheme 15 and described hereinafter in the Examples.

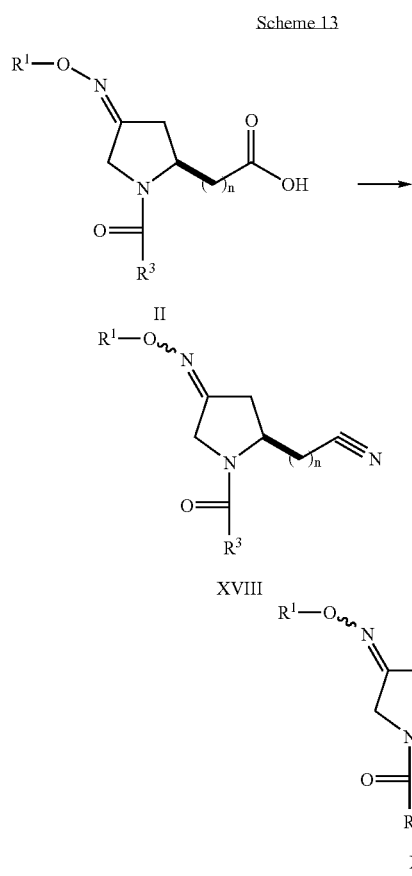

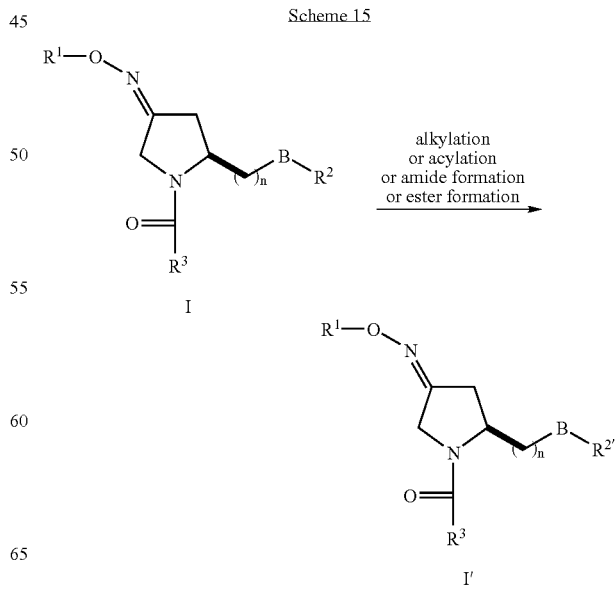

The reaction sequences outlined in the above Schemes provide enantiomerically pure compounds of formula I, if enantiomerically pure starting materials are used. (R)- as well as (S)-enantiomers can be obtained depending upon whether (R)- or (S)-forms of commercially available compounds of formulas IX and XI were used as the starting materials.

However, the reaction sequences outlined in the above Schemes usually provide mixtures of (E)- and (Z)-isomers with respect to the substituents on the exocyclic double bond of the pyrrolidine ring. In all cases studied, these (E)/(Z)-isomers could be separated by standard chromatography techniques well known to the person skilled in the art, such as by reversed phase high-pressure liquid chromatography (HPLC) or silica gel flash chromatography (FC). Alternatively, either one of the (E)/(Z)-isomers could successively be enriched by selective crystallisation in appropriate solvents or solvent mixtures. The assignment of the absolute configuration of the exocyclic double bond was performed using NMR-techniques well described in the literature as will be known to the practitioner skilled in the art (for configurational assignments of e.g. oxime functionalities (see e.g. E. Breitmaier, W. Voelter Carbon-13 NMR Spectroscopy, 3rd Ed, VCH, 1987, p. 240). In order to increase the overall yields of the preferred isomer (usually the (Z)-isomer), the less preferred isomer (usually the (E)-isomer) could be recycled by deliberate re-isomerization in organic solvents containing traces of acid, such as HCl, followed again by (E)/(Z)-separation through chromatography and/or crystallization, as illustrated in Scheme 16.

and Peter G. M. Wuts in "*Protective Groups in Organic Synthesis*", Wiley-Interscience, 1991.

Compounds of this invention can be isolated in association with solvent molecules by crystallization from evaporation of an appropriate solvent The pharmaceutically acceptable acid addition salts of the compounds of formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent Pharmaceutically acceptable base addition salts may be obtained in an analogous manner by treating a solution of compound of formula (I) with a suitable base. Both types of salt may be formed or interconverted using ion-exchange resin techniques.

EXAMPLES

The invention will be illustrated by means of the following examples that are not to be construed as limiting the scope of the invention.

The HPLC, NMR and MS data provided in the examples described below were obtained as followed. The following abbreviations are hereinafter used in the accompanying examples: min (min-ute), hr (hour), g (gram), mmol (millimole), m.p. (melting point), eq (equivalents), ml (milliliter), μl(microliters), Boc (butoxycarbonyl), CDCl$_3$ (deuterated chloroform), CDI (carbonyldiimidazole), DIC (Diisopropyl carbodiimide), DMAP (4Dimethylamino-pyridine), DMF

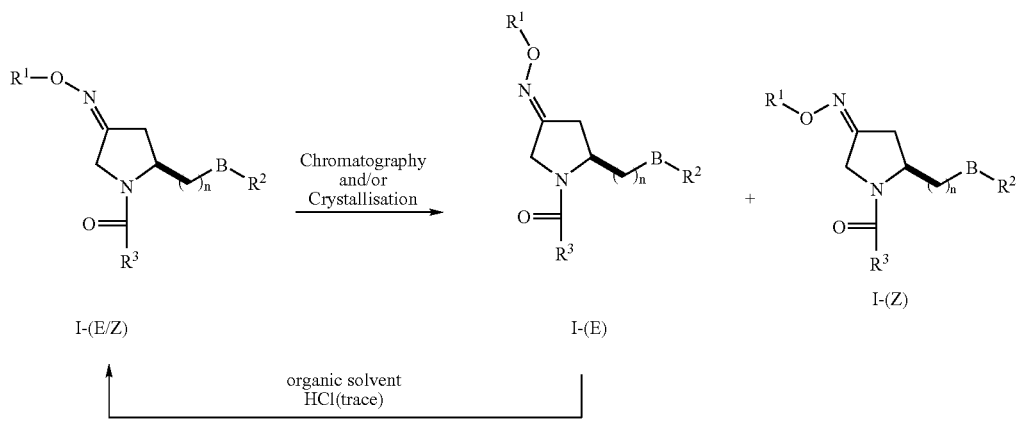

Scheme 16

If the above set out general synthetic methods are not applicable for obtaining compounds according to formula (I) and/or necessary intermediates for the synthesis of compounds of formula I, suitable methods of preparation known by a person skilled on the art should be used. In general, the synthesis pathways for any individual compound of formula (I) will depend on the specific substituents of each molecule and upon the ready availability of intermediates necessary; again such factors being appreciated by those of ordinary skill in the art. For all the protection, deprotection methods, see Philip J. Kocienski, in "*Protecting to Groups*", Georg Thieme Verlag Stuttgart New York 1994 and, Theodora W. Greene (Dimethylformamide), DMSO (Dimethylsulfoxide), DMSO-d$_6$ (deuterated dimethylsulfoxide), EDC (1-(3-Dimethyl-amino-propyl)-3-ethylcarbodiimide), HCl (acid chloride), HOBt (1-Hydroxybenzotriazole), K$_2$CO$_3$ (potassium carbonate), MgSO$_4$ (Magnesium sulfate), NaHCO$_3$ (Sodium bicarbonate), NaOH (Sodium hydroxide), Na$_2$SO$_4$ (Sodium sulfate), NH$_4$Cl (Ammonium chloride), NMM (N-methylmorpholine), Pd/C (Palladium on charcoal), TBDMS (t-butyldimethylsilyl)TFA (Trifluoroacetic acid).

The compounds of the present invention may be synthesized according to the different synthesis pathways provided above. The following examples illustrate preferred methods for synthesizing the compounds according to formula (I), and for determining their biological activities.

Intermediate 1 tert-butyl (2S,4R)-4-{[tert-butyl(dimethyl)silyl]oxy}-2-formyl pyrrolidine-1-carboxylate (cf Scheme 6, compound XII)

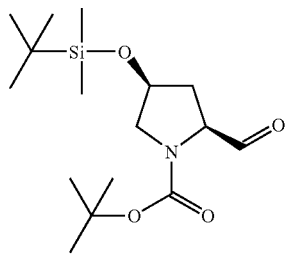

To a mixture of commercial (4R)-4-hydroxy-L-proline (75 g, 0.57 mol) in 10% NaOH (11) was added (Boc)$_2$O (186 g, 0.855 mol) at 0° C. with stirring. The reaction was allowed to stir at RT for 10 h and then washed with petroleum ether. The aqueous layer was acidified with citric acid to pH=4 and extracted with ethyl acetate. The combined organic layer was washed with brine and dried over Na$_2$SO$_4$. The solvent was removed under vacuum to give crude (4R)-1-(tert-butoxycarbonyl)-4-hydroxy-L-proline (118 g) as viscous liquid. Yield: 89%

To a solution of (4R)-1-tert-butoxycorbonyl)-4-hydroxy-L-proline (100 g, 0.432 mol) in dry DMF (600 ml), at 0° C. was added K$_2$CO$_3$ (179 g, 1.3 mol) followed by iodoethane (101 g, 0.65 mol). After stirring at RT for 12 h, K$_2$CO$_3$ was filtered off and DMF was distilled off under reduce pressure. The residue was diluted with dichloromethane (11), washed with brine and dried. The solvent was removed under vacuum to give crude 1-1-tert-butyl 2-ethyl(2S, 4R)-4-hydroxypyrrolidine-1,2-dicarboxylate (103 g) as yellow liquid. Yield: 91%

$^1$H NMR (300 MHz, CDCl$_3$): 1.25 (t, 3H), 1.4 (d, 9H), 1.9-2.2 (m, 2H), 2.5 (m, 1H), 3.5 (m, 2H), 4.2 (m, 2H), 4.4-4.6 (m, 2H).

To a solution of 1-tert-butyl 2-ethyl (2S,4R)-4-hydroxypyrrolidine-1,2-dicarboxylate (100 g, 0.38 mol) in dry dichloromethane (1.51) at 25° C. was added DMAP (47 g, 0.38 mol), followed by triethylamine (39 g, 0.38 mol). To the above reaction mixture was added TBDMSCl (64 g, 0.42 mol) dissolved in dry dichloromethane (200 ml) drop-wise over a period of 45 min. After stirring at RT for 20 h, the reaction mixture was diluted with water and separated the organic layer. The organic layer was washed with 5% aq. citric acid, brine and dried over Na$_2$SO$_4$. The solvent was removed under vacuum to give 1-tert-butyl 2-ethyl (2S,4R)-4-{[tert-butyl(dimethyl)silyl]oxy}pyrrolidine-1,2-dicarboxylate (140 g) as a colorless liquid. Yield: 97%

$^1$H NMR (300 MHz, CDCl$_3$): 0.0 (s, 6H), 0.8 (s, 9H), 1.2 (t, 3H), 1.45 (d, 9H), 1.7-1.9 (m, 2H), 2.2 (m, 1H), 3.3-3.5 (m, 2H), 4.2 (m, 2H), 4.5 (m, 1H).

To a suspension of lithium aluminium hydride (10 g) in dry tetrahydrofuran (750 ml) at −40° C. was added 1-tert-butyl 2-ethyl 1-tert-butyl 2-ethyl (2S,4R)-4-{[tert-butyl(dimethyl)silyl]oxy}pyrrolidine-1,2-dicarboxylate (100 g, 0.289 mol) drop-wise in tetrahydrofuran (250 ml). After stirring at −40° C. for 5 h, the reaction mixture was quenched with 10% NaOH (40 ml). Filtered off the solid residue, washed with tetrahydrofuran and the filtrate was evaporated under reduce pressure to give tert-butyl (2S,4R)-4-{[tert-butyl(dimethyl)silyl]oxy}-2-(hydroxymethyl) pyrrolidine-1-carboxylate (85 g) as a colorless liquid. Yield: 94%

LCMS: ESI+: 232 (M−Boc+H)$^+$, 276 (M−tBu+H)$^+$, 354 (M+Na)$^+$ $^1$H NMR (300 MHz, DMSO-d6): 0.05 (s, 6H), 0.78 (s, 9H), 1.33 (s, 9H), 1.65-2.00 (m, 2H), 3.20 (m, 2H), 3.38 (m, 2H), 3.70 (m, 1H), 4.30 (m, 1H), 4.60 (t, 1H).

To a mixture of DMSO (53 g, 0.68 mol) and oxalylchloride (43 g, 0.34 mol) in dry dichloromethane (1.51) at −78° C. was added tert-butyl (2S,4R)-4-{[tert-butyl(dimethyl)silyl]oxy}-2-(hydroxymethyl)pyrrolidine-1-carboxylate (75 g, 0.226 mol) drop-wise. After stiring at −78° C. for 1 h, was added triethylamine (158 ml, 1.13 mol) drop-wise and warmed the reaction mixture slowly to RT. The reaction mixture was diluted with water and separated the organic layer. The organic layer was washed with brine and dried. The solvent was removed under vacuum to give tert-butyl (2S,4R)-4-{[tert-butyl(dimethyl)silyl]oxy}-2-formylpyrrolidine-1-carboxylate (70 g) as pale yellow liquid. Yield: 94%

Intermediate 2

3-[(2R,4R)-4-hydroxypyrrolidin-2-yl]propanoic acid (cf Scheme 6, compound IXb)

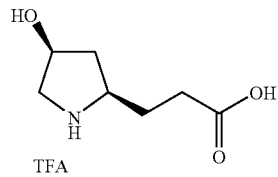

To a mixture of tert-butyl (2S,4R)-4-{[tert-butyl(dimethyl)silyl]oxy}-2-formyl pyrrolidine-1-carboxylate (Intermediate1, 40 g, 0.12 mol) in pyridine (250 ml) was added malonic acid (32 g, 0.303 mol) followed by pyrrolidine (0.5 ml) and heated to 50° C. for 4 h. Excess pyridine was distilled off under reduce pressure and residue was diluted with water. The mixture was extracted with dichloromethane, dried and concentrated under vacuum to give 3-((2S,4R)-1-tert-butoxycarbonyl)-4-{[tert-butyl(dimethyl) silyl]oxy}pyrrolidin-2-yl) acrylic acid (45 g). Yield: 98%

$^1$H NMR (300 MHz, CDCl$_3$): 0.0 (s, 6H), 0.75(s, 9H), 1.4 (d, 9H), 1.65 (m, 1H ), 1.9 (m, 1H), 3.3-3.6 (m, 2H), 4.2-4.4 (m, 2H), 5.9-6.0 (m, 1H), 6.9-7.1 (m, 1H).

To a solution of 3-((2S,4R)-1-(tert-butoxycarbonyl)-4-{[tert-butyl(dimethyl)silyl]oxy}-pyrrolidin-2-yl)acrylic acid (40 g, 0.107 mol) in dry DMF (250 ml) was added iodoethane (17.3 ml, 0.23 mol), followed by K$_2$CO$_3$ (29 g, 0.22 mol). After stirring at RT for 4 h, K$_2$CO$_3$ was filtered off and solvent removed under vacuum. The residue was taken in dichloromethane, washed with brine and dried. The solvent was removed under vacuum to give tert-butyl (2S,4R)-4-{[tert-butyl(dimethyl)silyl]oxy}-2-[(1E)-3-ethoxy-3-oxoprop-1-en-1-yl]pyrrolidine-1-carboxylate (35 g) as pale yellow liquid. Yield: 82%

A mixture of tert-butyl (2S,4R)-4-{[tert-butyl(dimethyl) silyl]oxy}-2-[(1E)-3-ethoxy-3-oxoprop-1-en-1-yl]pyrrolidine-1-carboxylate (35 g, 0.087 mmol)) and Pd/C (3.5 g) in ethyl acetate (400 ml) was hydrogenated under a pressure of 80 psi for 2 h. The reaction mixture was filtered off and filtrate concentrated under vacuum to give tert-butyl (2R,4R)-4-{

[tert-butyl(dimethyl)silyl]oxy}-2-(3-ethoxy-3-oxopropyl) pyrrolidine-1-carboxylate (28 g) as a liquid. Yield: 80%

A mixture of tert-butyl (2R,4R)-4-{[tert-butyl(dimethyl) silyl]oxy}-2-3-ethoxy-3-oxo-propl)pyrrolidine-1-carboxylate (25 g, 0.062 mol), NaOH (2.5 g, 0.062 mol), water and methanol (100 ml each) was stirred at RT for 8 h. The reaction mixture was evaporated under vacuum and residue neutralized with 5% citric acid The product was extracted into dichloromethane, dried and concentrated. The crude was purified by column chromatography over silica gel (petroleum ether/dichloromethane, 1:1) to give 3-((2R,4R)-1-(tert-butoxycarbonyl)-4-{[tert-butyl(dimethyl)silyl] oxy}pyrrolidin -2-yl)propanoic acid (17 g) as liquid. Yield: 65%

LCMS: ESI−: 372 (M−H)−; ESI+: 274 (M−Boc+H)+, 318 (M−tBu+H)+, 374 (M+H)+

¹H NMR (300 MHz, DMSO-d6): 0.04 (s, 6H), 0.83 (s, 9H), 1.37 (s, 9H), 1.60-2.20 (m, 6H), 2.90-3.50 (m, 3H), 3.78 (m, 1H), 4.31 (s, H), 12.02 (s, 1H).

To a solution of 3-((2R,4R)-1-(tert-butoxycarbonyl)-4-{[tert-butyl(dimethyl)silyl]oxy}-pyrrolidin-2-yl)propanoic acid (5.1 g, 13.65 mmol) in dichloromethane (100 ml) at 0° C. were added trifluoroacetic acid (14 ml) and water (3 ml). The reaction mixture was allowed to warm up and stirred overnight. The reaction mixture was concentrated in vacuo to afford 3-[(2R,4R)-4-hydroxypyrrolidin-2-yl]propanoic acid as TFA salt (3.74 g). Yield: 100%

¹H NMR (300 MHz, MeOD): 0.20 (m, 1H), 0.55 (m, 3H), 0.95 (m, 2H), 1.60-2.00 (m, 2H), 2.05-2.40 (m, 1H), 2.96 (m, 1H).

Intermediate 3

(2S,4R)-1-(biphenyl-4-ylcarbonyl)-4-hydroxypyrrolidin-2-yl acetic acid (cf Scheme 5, compound VIII)

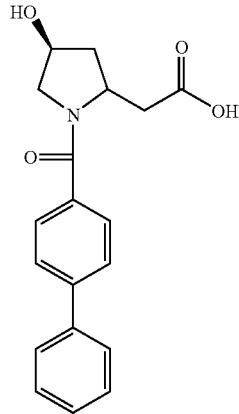

To a solution of commercial [(2R,4R)-4-hydroxypyrrolidin-2-yl]acetic acid hydrochloride (5.03 g, 27.69 mmol), triethylamine (11.32 g, 110.77 mmol) in water (16.5 ml) and tetrahydrofuran (25 ml) at 0° C. under argon was added drop wise a solution of the 4-phenyl-benzoyl chloride in dry tetrahydrofuran (25 ml). The reaction was allowed to warm to RT and stirred overnight The reaction mixture was concentrated and the crude product was acidified under stirring at 5° C. adding 100 ml of HCl 1N. The white suspension was stirred at 5° C. for 10 minutes, filtered off under vacuum, rinsed with HCl 1N and water. After drying under vacuum the still wet white solid was taken up in 14 ml of tetrahydrofuran and brought to reflux until dissolution, and hexane was added to precipitate the solid. The whole was allowed to cool down to RT under stirring for 5 minutes and was filtered off and rinsed with hexane to give [(2S,4R)-1-(biphenyl-4-ylcarbonyl)-4-hydroxypyrrolidin-2-yl] acetic acid as a white powder (4.344 g). Yield: 72%. HPLC purity: 84%

LCMS: ESI−: 280 (M−H−CO2)−; 324 (M−H)−; ESI+: 326 (M+H)+

¹H NMR (300 MHz, DMSO-d6): 1.82 (m, 1H), 2.11 (m, 1H), 2.5 (m, 1H), 2.81 (dd, J=15.6, J=3.2, 1H), 3.3 (m, 1H), 3.51 (dd, J=11.7, J=2.6, 1H), 4.16 (m, 1H),4.40 (m, 1H), 7.30-8.00 (m, 9H).

Intermediate 4

3-[(2R,4R)-1-(biphenyl-4-ylcarbonyl)-4-hydroxypyrrolidin-2-yl]propanoic acid (cf Scheme 5, compound VIII)

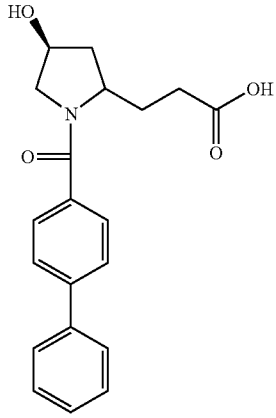

The same method as employed in the preparation of Intermediate 3, but starting from 3-[(2R,4R)-4-hydroxypyrrolidin-2-yl]propanoic acid (Intermediate 2), gave the title compound. Yield: 54%. HPLC purity: 96%

Intermediate 5

[(2S)-1-(biphenyl-4-ylcarbonyl)-4-oxopyrrolidin-2-yl]acetic acid (cf Scheme 4, compound IV)

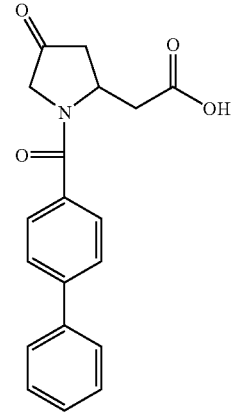

To a solution of the (2S,4R)-1-biphenyl-4-ylcarbonyl)-4-hydroxypyrrolidin-2-yl acetic acid (Intermediate 3, 4.00 g, 12.29 mmol) and triethylamine (8.70 g, 22.13 mmol) in 16 ml of dry DMSO at 2° C. under argon was added a solution of Pyr.SO₃ (3.52 g, 22.13 mmol) in 32 ml of dry DMSO and the reaction warmed to RT and stirred overnight. The reaction was quenched adding HCl 3N (70 ml) followed by ethyl acetate and hexane. The aqueous phase were extracted twice with ethyl acetate/ hexane (1/1). Combined organic phases were dried over MgSO4, filtered and concentrated under vacuum to give [(2S)-1-(biphenyl-4-yl-carbonyl)-4-oxopyrrolidin-2-yl]acetic acid as brown oil (1.51 g). Yield: 38%. HLPC purity: 76%

¹H NMR (300 MHz, CDCl₃): 2.50-3.27 (m, 4H), 3.67-4.28 (m, 2H), 5.16 (m, 1H), 7.30-7.60 (m, 9H).

Intermediate 6

3-[(2R)-1-(biphenyl-4-ylcarbonyl)-4-oxopyrrolidin-2-yl]propanoic acid (cf Scheme 4, compound IV)

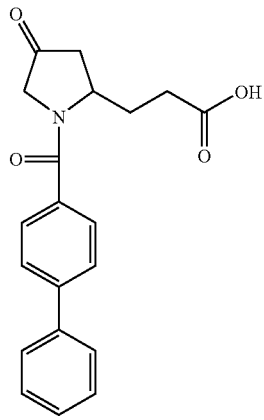

The same method as employed in the preparation of Intermediate 5, but starting from 3-[(2R,4R)-1-(biphenyl-4-ylcarbonyl)-4-hydroxypyrrolidin-2-yl]propanoic acid (Intermediate 4), gave the title compound. Yield: 20%. HLPC purity: 82%

LCMS: ESI−: 336 (M−H)⁻; ESI+: 338 (M+H)⁺

¹H NMR (300 MHz, CDCl₃): 1.71-2.16 (m, 3H), 2.33-2.66 (m, 3H), 3.97 (m, 2H), 5.17 (m, 1H), 7.30-7.70 (m, 9H), 8.01 (s, 1H).

Intermediate 7

[(2S,4EZ)-1-(biphenyl-4-ylcarbonyl)-4-(methoxyimino)pyrrolidin-2-yl] acetic acid (cf Scheme 2, compound II)

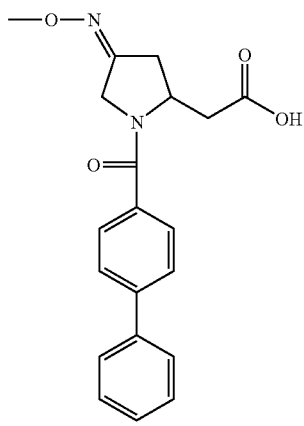

A solution of [(2S)-1-(biphenyl-4-ylcarbonyl)-4-oxopyrrolidin-2-yl]acetic acid (Intermediate 5, 1.50 g, 6.64 mmol), hydroxylamine methyl ether hydrochloride (0.58 g, 6.96 mmol) and triethylamine (1.62 ml, 11.60 mmol) in chloroforme (30 ml) was stirred at RT for 2 days Solvent was removed under reduced pressure and the residue was taken up in ethyl acetate. Organic phase was washed twice with a solution of citric acid 10% and once with brine. Organic phase was then dried on MgSO4, filtered, and concentrated to give [(2S,4EZ)-1-(biphenyl-4-ylcarbonyl)-4-(methoxyimino)pyrrolidin-2-yl]acetic acid as a cream solid (1.14 g). Yield: 45%. HLPC purity: 92%

LCMS: ESI−: 277 (M−OMe−CO₂−H)⁻, 307 (M−CO₂−H)⁻, 321 (M−OMe−H)⁻, 351 (M−H)⁻; ESI+: 335 (M−H₂O+H)⁺, 353 (M+H)⁺

¹H NMR (300 MHz, CDCl₃): 2.20-3.50 (m, 4H), 3.74 (s, 3H), 3.90-4.50 (m, 2H), 4.80 (m, 1H), 7.30-7.70 (m, 9H).

Intermediate 8

3-[(2R,4EZ)-1-(biphenyl-4-ylcarbonyl)-4-(methoxyimino)pyrrolidin-2-yl]propanoic acid (cf Scheme 2, compound II)

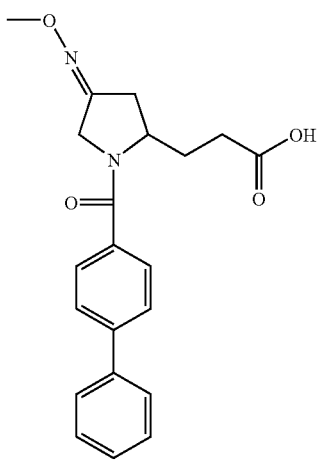

The same method as employed in the preparation of Intermediate 7, but starting from 3-[(2R)-1-(biphenyl-4-ylcarbonyl)-4-oxopyrrolidin-2-yl]propanoic acid (Intermediate 6), gave the title compound. Yield: 43%. HLPC purity: 92%

LCMS: EST−: 291 (M−OMe−CO₂−H)⁻, 335 (M−OMe−H)⁻, 365 (M−H)⁻, ESI+: 367 (M+H)⁺

¹H NMR (300 MHz, CDCl₃): 1.70-2.10 (m, 2H), 2.30-3.00 (m, 4H), 3.87 (s, 3H), 4.00-4.50 (m, 2H), 5.00 (m, 1H), 7.30-7.70 (m, 9H).

Example 1 methyl [(2S,4EZ)-1-(biphenyl-4-ylcarbonyl)-4-(methoxyimino)pyrrolidin-2-yl]acetate

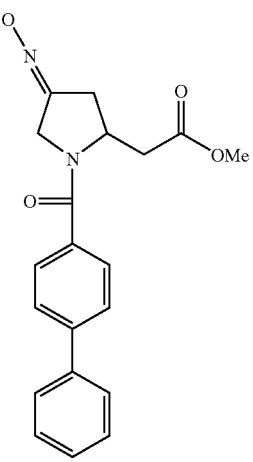

To a solution of [(2S,4R)-1-biphenyl-4-ylcarbonyl)-4-hydroxypyrrolidin-2-yl]acetic acid (Intermediate 3, 350 mg, 1.08 mmol) in toluene-methanol (10 ml, 1-1) was added (diazomethyl)trimethylsilane (2.76 ml, 2M in hexane). After 3 hours, the reaction mixture was concentrated and purified by silica gel column chromatography (ethyl acetate) to give methyl [(2S,4R)-1-(biphenyl-4-ylcarbonyl)-4-hydroxypyrrolidin-2-yl]acetate (256 mg). Yield: 70%. HPLC purity: 98%

LCMS: ESI+: 340 (M+H)⁺

¹H NMR (300 MHz, DMSO-d6): 1.82 (m, 1H), 2.11 (m, 1H), 2.6 (dd, J=15.4, J=8.3, 1H), 2.97 (dd, J=15.3, J=3.4, 1H), 3.25 (d, J=11.4, 1H), 3.62 (s, 3H), 3.67 (dd, J=11.4, J=3.4, 1H), 4.16 (m, 1H), 4.44 (m, 1H), 4.86 (d, J=3.4, OH) 7.30-8.00 (m, 9H).

A solution of DMSO (31.4 µl, 0.44 mmol) in dichloromethane (1 ml) was added drop wise to a solution of oxalyl chloride (19 µl, 0.22 mmol) in dichloromethane (2 ml) at −78° C. under argon. After 15 min at −78° C., A solution of methyl [(2S,4R)-1-(biphenyl-4-ylcarbonyl)-4-hydroxypyrrolidin-2-yl]acetate (50 mg, 0.15 mmol) in dichloromethane (1 ml) was added drop wise. The reaction mixture was stirred at −78° C. for 1 hour and triethylamine (0.102 ml, 0.74 mmol) was added and allowed to warm to room temperature. The reaction mixture was diluted with ethyl acetate, washed with water then brine. The organic phase was dried (MgSO4) and concentrated to afford the methyl [(2S)-1-(biphenyl-4-ylcarbonyl)-4-oxopyrrolidin-2-yl]acetate (66 mg). Yield: 100%. HPLC purity: 99%

LCMS: ESI−: 336 (M−H)⁻, ESI+: 338 (M+H)⁺

$^1$H NMR (300 MHz, CDCl$_3$): 2.55 (m, 1H), 2.70 (m, 1H), 2.87 (m, 1H), 3.07 (m, 1H), 3.69 (s, 3H), 3.85 (m, 1H), 4.14 (m, 1H), 5.12 (m, 1H), 7.20-8.00 (m, 9H).

A solution of methyl [(2S)-1-(biphenyl-4-ylcarbonyl)-4-oxopyrrolidin-2-yl]acetate (43 mg, 0.13 mmol), hydroxylamine methyl ether hydrochloride (32 mg, 0.38 mmol) and triethylamine (53 µl, 0.38 mmol) in chloroforme (3 ml) was stirred at 70° C. for 5 days. The reaction mixture was diluted with dichloromethane and washed with HCl 1N. The organic phase was dried (MgSO$_4$) and concentrated to afford methyl [(2S,4EZ)-1-(biphenyl-4-yl-carbonyl)--4-(methoxyimino) pyrrolidin-2-yl]acetate (40 mg). Yield: 62%. HPLC purity: 94%

.LCMS: ESI+: 367 (M+H)⁺

$^1$H NMR (300 MHz, CDCl$_3$): 2.66 (m, 3H), 2.95 (m, 1H), 3.67 (s, 3H), 3.82 (s, 3H), 4.14 (m, 1H), 4.30 (m, 1H), 5.01 (m, 1H), 7.20-8.00 (m, 9H).

Example 2 methyl 3-[(2R,4EZ)-1-biphenyl-4-ylcarbonyl)-4-(methoxyimino)pyrrolidin-2-yl]propanoate

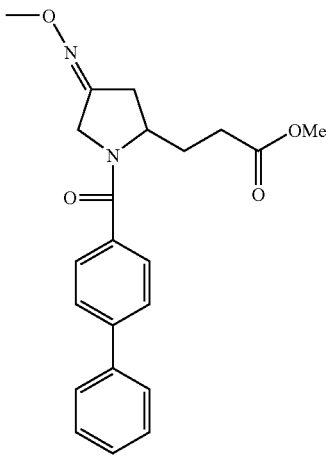

To a solution of 3-[(2R,4EZ)-1-(biphenyl-4-ylcarbonyl)-4-(methoxyimino)pyrrolidin-2-yl]propanoic acid (Intermediate 8, 20 mg, 0.05 mmol) in toluene-methanol (1 ml, 3-1) was added (diazomethyl)trimethylsilane (0.110 ml, 2M in hexane). After 3 hours, the reaction mixture was concentrated and purified by silica gel column chromatography (ethyl acetate) to give methyl 3-[(2R,4EZ)-1-(biphenyl-4-ylcarbonyl)-4-(methoxyimino)pyrrolidin-2-yl]propanoate (20 mg). Yield: 96%. HPLC purity: 94%

LCMS: ESI+: 381 (M+)⁺

$^1$H NMR (300 MHz, CDCl$_3$): 2.01 (m, 2H), 2.20-3.00 (m, 4H), 3.69 (s, 3H),3.86 (s, 3H), 4.31 (m, 2H), 4.97 (m, 1H), 7.20-7.75 (m, 9H).

Example 3 cyclopentyl [(2S,4EZ)-1-(biphenyl-4-ylcarbonyl)-4-(methoxyimino)pyrrolidin-2-yl]acetate

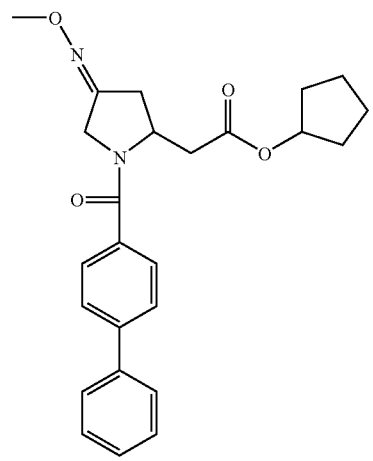

To a solution of [(2S,4EZ)-1-(biphenyl-4-ylcarbonyl)-4-(methoxyimino)pyrrolidin-2-yl]acetic acid (Intermediate 7, 25 mg, 0.07 mmol) in dichloromethane (1 ml) were added EDC (14 mg, 0.07 mmol), DMAP (3 mg, 0.02 mmol) and cyclopentanol (6 mg, 0.07 mmol). The reaction mixture was stirred overnight. The organic phase was washed with NH$_4$Cl, NaHCO$_3$ then brine. The organic phase was dried (MgSO$_4$) and concentrated to afford cyclopentyl [(2S,4EZ)-1-biphenyl-4-ylcarbonyl)-4-(methoxyimino)pyrrolidin-2-yl]acetate (25 mg). Yield: 78%. HPLC purity: 94%

LCMS: ESI+: 421 (M+)⁺

$^1$H NMR (300 MHz, CDCl$_3$): 1.50-2.01 (m, 8H), 2.50-3.10 (m, 4H), 3.85 (s, 3H), 4.25 (m, 2H), 5.18 (m, 1H), 5.30 (m, 1H), 7.20-7.75 (m, 9H).

Example 4 cyclopentyl 3-[(2R,4EZ)-1-(biphenyl-4-ylcarbonl)-4-(methoxyimino)pyrrolidin-2-yl]propanoate

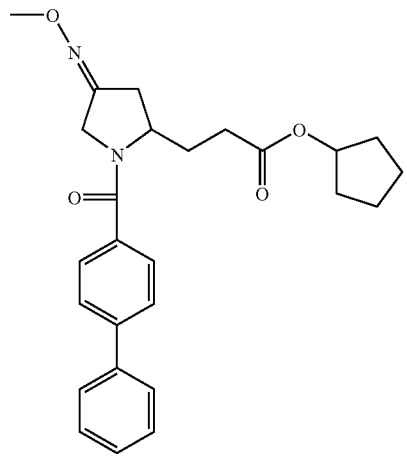

The same method as employed in the preparation of Example 3, but starting from 3-[(2R,4EZ)-1-biphenyl-4-yl-carbonyl)-4-(methoxyimino)pyrrolidin-2-yl]propanoic acid (Intermediate 8), gave the title compound. Yield: 81%. HPLC purity: 92%

LCMS: ESI+: 420 (M−Me+H)+, 435 (M+H)+

$^1$H NMR (300 MHz, CDCl$_3$): 1.50-2.01 (m, 10H), 2.20-3.00 (m, 4H), 3.86 (s, 3H), 4.31 (m, 2H), 4.92 (m, 1H), 5.16 (m, 1H), 7.20-7.75 (m, 9H).

Example 5

2-[(2S,4EZ)-1-(biphenyl-4-ylcarbonyl)-4-(methpoxyimino)pyrrolidin-2-yl]-N-[2S)-2-hydroxy-2-phenylethyl]acetamide

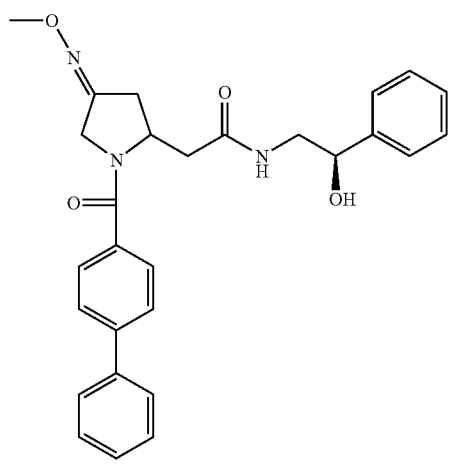

To a solution of [(2S,4EZ)-1-(biphenyl-4-ylcarbonyl)-4-(methoxyimino)pyrrolidin-2-yl]acetic acid (Intermediate 7, 25 mg, 0.07 mmol) in tetrahydrofuran (1 ml) at −25° C. were added NMM (18 mg, 0.18 mmol) followed by isobutyl chloroformate (10 mg, 0.07 mmol). The reaction mixture was stirred 10 min then a solution of (S)-2-amino-1-phenylethanol (10 mg, 0.07 mmol) in tetrahydrofuran (1 ml). The reaction was allowed to warm up to room temperature and was stirred overnight. Dichloromethane was added and the organic phase was washed with NH$_4$Cl, NaHCO$_3$ then brine. The organic phase was dried (MgSO$_4$) and concentrated to afford 2-[(2S,4EZ)-1-(biphenyl-4-ylcarbonyl)-4-(methoxyimino) pyrrolidin-2-yl]-N-[(2S)-2-hydroxy-2-phenylethyl] acetamide (35 mg). Yield: 94%. HPLC purity: 90%

LCMS: ESI−: 470 (M−H)−, ESI+: 422 (M−H$_2$O−MeOH+ H)+, 454 (M−H$_2$O+H)+, 472 (M+M)+

$^1$H NMR (300 MHz, CDCl$_3$): 2.66 (m, 3H), 2.88 (m 2H), 3.17 (m, 1H), 3.82 (s, 3H), 4.14 (m, 1H), 4.40 (m, 1H), 4.76 (m, 1H), 5.10 (m, 1H), 7.20-7.75 (m, 14H).

Example 6

3-[(2R,4EZ)-1-(biphenyl-4-ylcarbonyl)-4-(methoxyimino)pyrrolidin-2-yl]-N-[(2S)-2-hydroxy-2-phenylethyl]propanamide

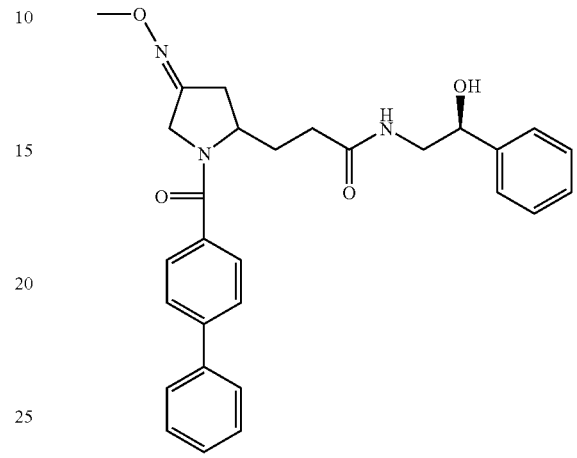

The same method as employed in the preparation of Example 5, but starting from 3-[(2R,4EZ)-1-(biphenyl-4-ylcarbonyl)-4-(methoxyimino)pyrrolidin-2-yl]propanoic acid (Intermediate 8), gave the title compound. Yield: 52%. HPLC purity: 95%

LCMS: ESI−: 484 (M−H)−; ESI+: 436 (M−H$_2$O−MeOH+ H)+, 468 (M−H$_2$O+H)+, 486 (M+n)+

$^1$H NMR (300 MHz, CDCl$_3$): 1.88 (m, 2H), 2.47 (m, 3H), 2.87 (m, 1H), 3.49 (m, 2H), 3.85 (s, 3H), 4.14 (m, 1H), 4.38 (m, 1H), 4.67 (m, 1H), 4.96 (m, 1H), 7.20-7.75 (m, 14H).

Example 7

2-[(2S,4EZ)-1-(biphenyl-4-ylcarbonyl)-4-(methoxyimino)pyrrolidin-2-yl]acetamide

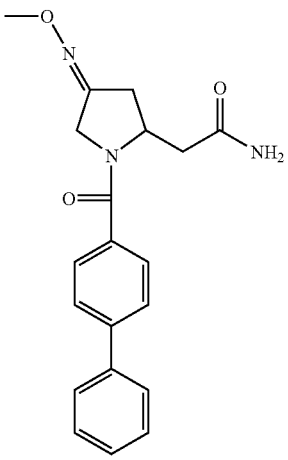

To a solution of [(2S,4EZ)-1-(biphenyl-4-ylcarbonyl)-4-(methoxyimino)pyrrolidin-2-yl]acetic acid (intermediate 7, 50 mg, 0.14 mmol) in tetrahydrofuran (4 ml) were added HOBt (29 mg, 0.21 mmol), EDC (41 mg, 0.21 mmol), DMAP (2 mg, 0.01 mmol) followed by ammonia in dioxane (0.425 ml, 2M, 0.21 mmol). The reaction mixture was stirred overnight Ethyl acetate was added and the organic phase was washed with citric acid 5%, NH$_4$Cl, NaHCO$_3$ then brine. The organic phase was dried (MgSO$_4$) and concentrated to afford 2-[(2S,4EZ)-1-(biphenyl-4-ylcarbonyl)-4-(methoxyimino)pyrrolidin-2-yl]acetamide (40 mg). Yield: 81%. HPLC purity: 93%

LCMS: ESI+: 320 (M−MeOH+H)$^+$, 374 (M+Na)$^+$ $^1$H NMR (300 MHz, CDCl$_3$): 1.90 (m, 2H), 2.60-3.05 (m, 4H), 3.83 (s, 3H), 4.05-4.50 (m, 2H), 5.05 (m, 1H), 7.20-7.75 (m, 9H).

Example 8

3-[(2R,4EZ)-1-(biphenyl-4-ylcarbonyl)-4-(methoxyimino)pyrrolidin-2-yl]propanamide

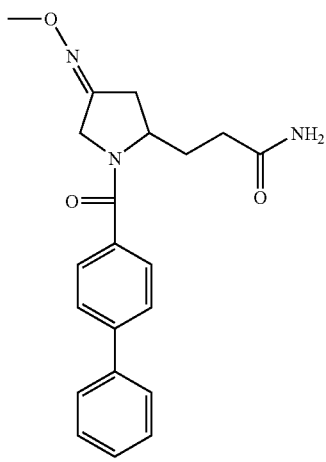

The same method as employed in the preparation of Example 7, but starting from 3-[(2R,4EZ)-1-(biphenyl-4-ylcarbonyl)-4-(methoxyimino)pyrrolidin-2-yl]propanoic acid (Intermediate 8), gave the title compound. Yield: 83%. HPLC purity: 90%

LCMS: ESI+: 334 (M−MeOH+H)$^+$, 351 (M−Me+H)$^+$, 366 (M+H)$^+$ $^1$H NMR (300 MHz, CDCl$_3$): 1.84 (m, 2H), 2.20-2.85 (m, 4H), 3.83 (s, 3H), 4.05-4.50 (m, 2H), 4.98 (m, 1H), 7.20-7.75 (m, 9H).

Example 9

(3EZ,5S)-1-(biphenyl-4-ylcarbonyl)-5-(2-morpholin-4-yl-2-oxoethyl) pyrrolidin-3-one O-methyloxime

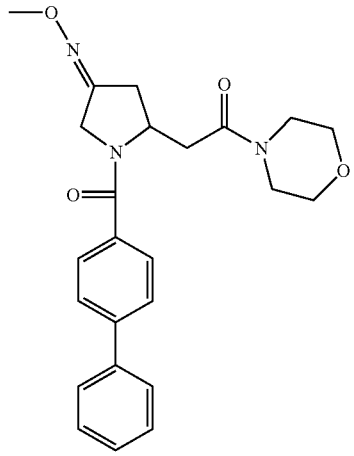

The same method as employed in the preparation of Example 7, but starting from [(2S,4EZ)-1-(biphenyl-4-ylcarbonyl)-4-(methoxyimino)pyrrolidin-2-yl]acetic acid (Intermediate 7) and morpholine, gave the title compound. Yield: 98%. HPLC purity: 100%

LCMS: EST+:390 (M−MeOH+H)$^+$, 422 (M+H)$^+$ $^1$H NMR (300 MHz, CDCl$_3$): 2.50-3.15 (m, 4H), 3.30-3.75 (m, 8H), 3.84 (s, 3H), 4.10 (m, 1H), 4.42 (m, 1H), 4.99 (m, 1H), 7.30-7.75 (m, 9H).

Example 10

(3EZ,5R)-1-(biphenyl-4-ylcarbonyl)-5-(3-morpholin-4-yl-3-oxopropyl) pyrrolidin-3-one O-methyloxime

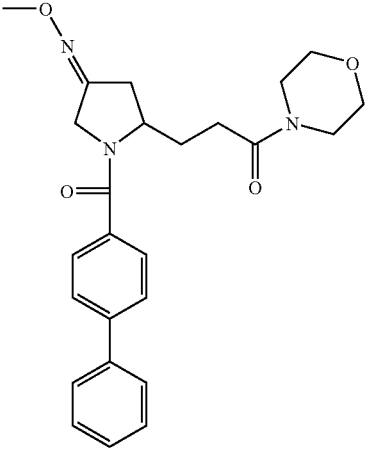

The same method as employed in the preparation of Example 7, but starting from 3-[(2R,4EZ)-1-(biphenyl-4-ylcarbonyl)-4-(methoxyimino)pyrrolidin-2-yl]propanoic acid (Intermediate 8) and morpholine, gave the title compound. Yield: 97%. HPLC purity: 96%

LCMS : EST+: 404 (M−MeOH+H)$^+$, 421 (M−Me+H)$^+$, 436 (M+H)$^+$ $^1$H NMR (300 MHz, CDCl$_3$): 1.70-2.95 (m, 6H), 3.30-3.75 (m, 8H), 3.84 (s, 3H), 4.10 (m, 1H), 4.42 (m, 1H), 4.99 (m, 1H), 7.30-7.75 (m, 9H).

Example 11

N-(2-aminophenyl)-2-[(2S,4EZ)-1-(biphenyl-4-yl-carbonyl)-4-(methoxy imino)pyrrolidin-2-yl] acetamide

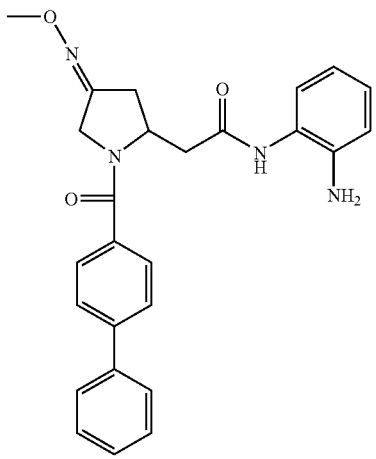

To a solution of [(2S,4EZ)-1-(biphenyl-4-ylcarbonyl)-4-(methoxyimino)pyrrolidin-2-yl]acetic acid (Intermediate 7, 30 mg, 0.09 mmol), 1,2-benzenediamine (9 mg, 0.09 mmol) and DMAP (16 mg, 0.13 mmol) in dichloromethane (2 ml) at 0° C. was added EDC (16 mg, 0.09 mmol). The reaction was allowed to warm up to room temperature and was stirred for 2 days. The solvent was removed in vacuo and the crude was purified by silica gel column chromatography (Ethyl acetate/cyclohexane, 80:20) to afford N-(2-aminophenyl)-2-[(2S, 4EZ)-1-(biphenyl-4-ylcarbonyl)-4-methoxyimino)pyrrolidin-2-yl]acetamide (26 mg). Yield: 63%. HPLC purity: 90%

LCMS: ESI-: 441 (M-H)$^-$; ESI+: 443 (M+H)$^+$, 465 (M+Na)$^+$ $^1$H NMR (300 MHz, CDCl$_3$): 2.55-3.20 (m, 4H), 3.82 (s, 3H), 4.11 (m, 1H), 4.49 (m, 1H), 5.37 (m, 1H), 7.10 (m, 2H), 7.30-7.75 (m, 11H).

Example 12

N-(2-aminophenyl)-3-[(2R,4EZ)-1-(biphenyl-4-yl-carbonyl)-4-(methoxy imino) pyrrolidin-2-yl] propanamide

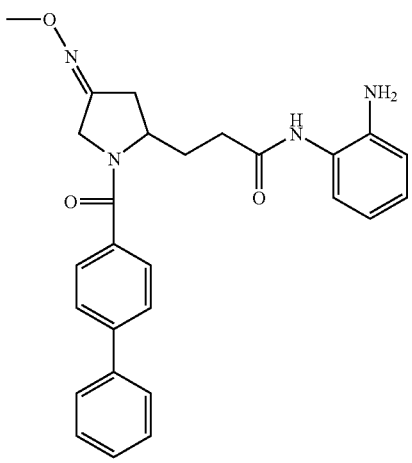

The same method as employed in the preparation of Example 11, but starting from 3-[(2R,4EZ)-1-(biphenyl-4-ylcarbonyl)-4-(methoxyimino)pyrrolidin-2-yl]propanoic acid (Intermediate 8), gave the title compound Yield. 54%. HPLC purity: 100%

LCMS: ESI-: 455 (M-H)$^-$; ESI+: 442 (M-Me+H)$^{+,}$ 457 (M+H)+, 479 (M+Na)$^+$ $^1$H NMR (300 MHz, CDCl$_3$): 1.50-3.00 (m, 6H), 3.81 (s, 3H), 4.13 (m, 1H), 4.33 (m, 1H), 5.08 (m, 1H), 6.74 (m, 1H), 6.91 (m, 1H), 7.30-7.65 (m, 11H).

Example 13

(3EZ,5S)-5-(1H-benzimidazol-2-ylmethyl-1-(biphenyl-4-ylcarbonyl) pyrrolidin-3-one O-methyloxime

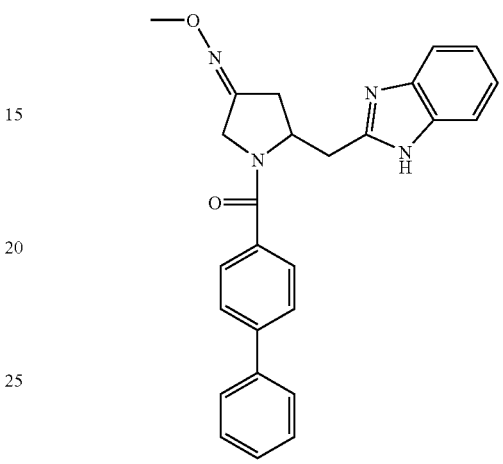

A solution of N-(2-aminophenyl)-2-[(2S,4EZ)-1-(biphenyl-4-ylcarbonyl)-4-(methoxy imino)pyrrolidin-2-yl]acetamide (Example 11, 21 mg, 0.05 mmol) and acetic acid (0.1 ml) in dichloromethane (1 ml) was stirred overnight. The organic phase was washed with NaHCO$_3$. The organic phase was dried (MgSO$_4$) and concentrated to afford (3EZ,5S)-5-(1H-benzimidazol-2-ylmethyl)-1-(biphenyl-4-ylcarbonyl) pyrrolidin-3-one O-methyloxime (14 mg). Yield: 65%. HPLC purity: 93%

LCMS: ESI-: 423 (M-H)$^-$; ESI+: 393 (M-MeOH+H)$^+$, 465 (M+Na)$^+$ $^1$H NMR (300 MHz, CDCl$_3$): 2.98 (m, 2H), 3.45 (m, 2H), 3.82 (s, 3H), 4.18 (m, 1H), 4.44 (m, 1H), 5.35 (m, 1H), 7.18 (m, 2H), 7.30-7.75 (m, 11H).

Example 14

(3EZ,5H)-5-[2-(1H-benzimidazol-2-yl)ethyl-]1-(biphenyl-4-ylcarbonyl) pyrrolidin-3-one O-methyloxime

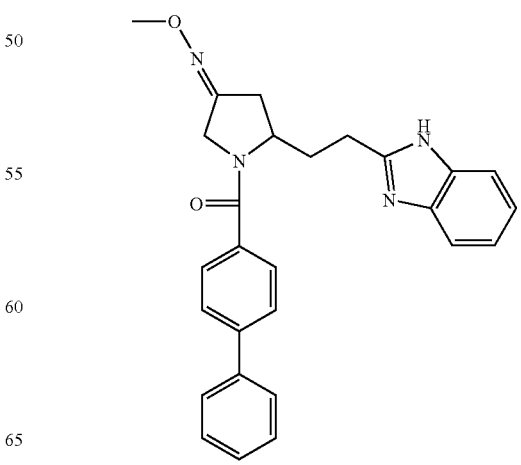

The same method as employed in the preparation of Example 11, but starting from H-(2-aminophenyl)-3-[(2R,4EZ)-1-(biphenyl-4-ylcarbonyl)-4-(methoxy imino) pyrrolidin-2-yl]propanamide (Example 12), gave the title compound. Yield: 51%. HPLC purity: 89%

LCMS: ESI−: 437 (M−H)−; ESI+: 439 (M+H)+

$^1$H NMR (300 MHz, CDCl$_3$): 2.00-3.35 (m, 6H), 3.84 (s, 3H), 4.05-4.55 (m, 2H), 4.99 (m, 1H), 7.15-7.75 (m, 13H).

Example 15

(3EZ,5S)-1-(biphenyl-4-ylcarbonyl-5-[(3-methyl-1,2,4-oxadiazol-5-yl)methyl] pyrrolidin-3-one O-methyloxime

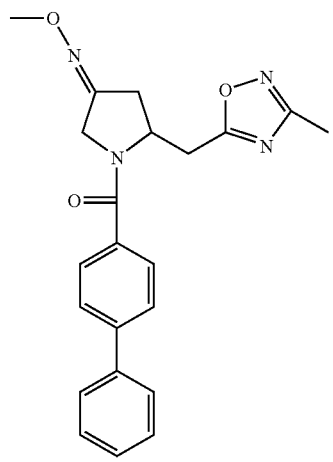

To a solution of [(2S,4EZ)-1-biphenyl-4-ylcarbonyl)-4-(methoxyimino)pyrrolidin-2-yl]acetic acid (Intermediate 7, 50 mg, 0.14 mmol) in dichloromethane (3 ml) was added N'-hydroxyethanimidamide (12 mg, 0.16 mmol) followed by DIC (36 mg, 0.28 mmol). The reaction mixture was stirred 1 h30. The precipitate was filtered and the solution was concentrated in vacuo. Pyridine (1 ml) was added and the reaction mixture was stirred at reflux overnight The solvent was removed and dichloromethane was added. The organic phase was washed with HCl 1N then NaHCO$_3$. The organic phase was dried (MgSO$_4$), concentrated and purified on silica gel column chromatography (Ethyl acetate/cyclohexane, 40:60) to afford (3EZ,5S)-1-(biphenyl-4-ylcarbonyl)-5-[(3-methyl-1,2,4oxadiazol-5-yl)methyl]pyrrolidin-3-one O-methyloxime (56 mg). Yield: 91%. HPLC purity: 90%

LCMS: ESI−: 389 (M−H)−; ESI+: 359 (M−MeOH+H)+, 391 (M+H)+

$^1$H NMR (300 MHz, CDCl$_3$): 2.39 (s, 3H), 2.65-3.10 (m, 2H), 3.27 (m, 2H), 3.83 (s, 3H), 4.20 (m, 2H), 5.15 (m, 1H), 7.30-7.75 (m, 9H).

Example 16

(3EZ,5H)-1-biphenyl-4-ylcarbonyl)-5-[2-(3-methyl-1,2,4-oxadiazol-5-ylethyl]pyrrolidin-3-one O-methyloxime

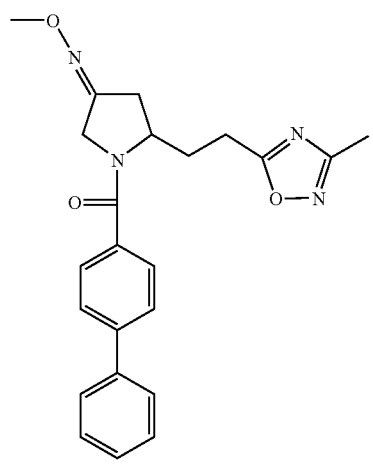

The same method as employed in the preparation of Example 15, but starting from 3-[(2R,4EZ)-1(biphenyl-4-ylcarbonyl)-4-(methoxyimino)pyrrolidin-2-yl]propanoic acid (Intermediate 8), gave the title compound. Yield: 81%. HPLC purity: 85%

LCMS: ESI+: 373 (M−MeOH+H)+, 405 (M+H)+

$^1$H NMR (300 MHz, CDCl$_3$): 2.00-3.10 (m, 6H), 2.16 (s, 3H), 3.85 (s, 3H), 4.05-4.55 (m, 2H), 5.05 (m, 1H), 7.30-7.75 (m, 9H).

Example 17

(3EZ,5S)-1-biphenyl-4-ylcarbonyl)-5-{[3-(2-hydroxyethyl)-1,2,4 oxadiazol-5-yl]methyl}pyrrolidin-3-one O-methyloxime

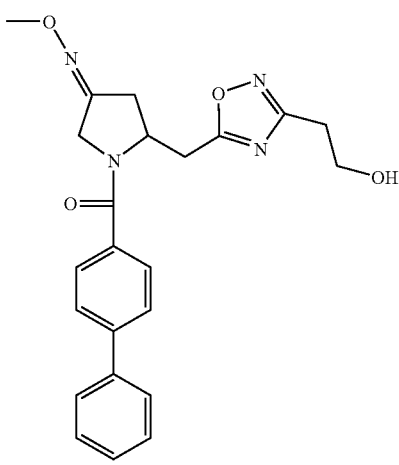

To a solution of [(2S,4EZ)-1-(biphenyl-4-ylcarbonyl)-4-(methoxyimino)pyrrolidin-2-yl]acetic acid (Intermediate 7, 50 mg, 0.14 mmol) in tetrahydrofuran (2 ml) was added CDI (37 mg, 0.23 mmol). The reaction mixture was stirred 1 h30.

A solution of N',3-dihydroxypropanimidamide (16 mg, 0.16 mmol), pyridine (34 ml, 0.14 mmol) in tetrahydrofuran was then added and the reaction mixture was stirred at reflux overnight The solvent was removed and ethyl acetate was added. The organic phase was washed with citric acid 5%, NH$_4$Cl, NaHCO$_3$ then brine. The organic phase was dried (MgSO$_4$), concentrated and purified on silica gel column chromatography (Ethyl acetate) to afford (3EZ,5S)-1-(biphenyl-4-ylcarbonyl)-5-{[3-(2-hydroxyethyl)-1,2,4-oxadiazol-5-yl]methyl}pyrrolidin-3-one O-methyloxime (19 mg). Yield: 27%. HPLC purity: 94%

LCMS: ESI−: 419 (M−H)$^-$; ESI+: 389 (M−MeOH+H)$^+$, 421 (M+H)$^+$ $^1$H NMR (300 MHz, CDCl$_3$): 2.70-3.50 (m, 6H),3.82 (s, 3H), 3.94 (m, 2H),4.11 (m, 1H), 4.31 (m, 1H), 5.30 (m, 1H), 7.30-7.75 (m, 9H).

Example 18

(3EZ,5R)-1-(biphenyl-4-ylcarbonl)-5-{2-[3-(2-hydroxyethyl)-1,2,4-oxadiazol-5-yl]ethyl}pyrrolidin-3-one O-methyloxime

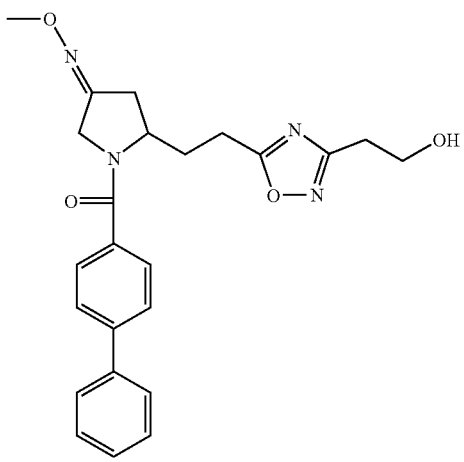

The same method as employed in the preparation of Example 17, but starting from 3-[(2R,4EZ)-1-(biphenyl-4-ylcarbonyl)-4-(methoxyimino)pyrrolidin-2-yl]propanoic acid (Intermediate 8), gave the title compound. Yield: 37%. HPLC purity: 96%

LCMS: ESI+: 403 (M−MeOH+H)$^+$, 420 (M−Me+H)$^+$, 435 (M+H)$^+$ $^1$H NMR (300 MHz, CDCl$_3$): 2.00-3.10 (m, 8H), 3.85 (s, 3H), 3.97 (m, 2H), 4.05-4.55 (m, 2H), 5.03 (m, 1H), 7.30-7.75 (m, 9H).

Example 19

Preparation of a Pharmaceutical Formulation

The following Formulation examples illustrate representative pharmaceutical compositions according to the present invention being.

Formulation 1—Tablets

A pyrrolidine compound of formula (I) is admixed as a dry powder with a dry gelatin binder in an approximate 1:2 weight ration. A minor amount of magnesium stearate is added as a lubricant The mixture is formed into 240-270 mg tablets (80-90 mg of active pyrrolidine compound per tablet) in a tablet press.

Formulation 2—Capsules

A pyrrolidine compound of formula (I) is admixed as a dry powder with a starch diluent in an approximate 1:1 weight ratio. The mixture is filled into 250 mg capsules (125 mg of active pyrrolidine compound per capsule).

Formulation 3—Liquid

A pyrrolidine compound of formula (I) (1250 mg), sucrose (1.75 g) and xanthan gum (4 mg) are blended, passed through a No.10 mash U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A pyrrolidine compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active pyrrolidine compound) in a tablet press.

Formulation 5—Injection

A pyrrolidine compound of formula (I) is dissolved in a buffered sterile saline injectable aqueous medium to a concentration of approximately 5 mg/ml.

Example 20

Biological Assays

The compounds according to formula (I) may be subjected to the following assays:
  a) In Vitro Competition Binding Assay on hOT Receptor with Scintillation Proximity Assay (11).

This assay allows to determine the affinity of the test compounds for the human Oxytocin (hOT) receptor. Membranes from HEK293EBNA (cells expressing the hOT receptor) were suspended in buffer containing 50 mM Tris-HCl, pH 7.4, 5 mM MgCl2 and 0.1% BSA (w/v). The membranes (2-4 μg) were mixed with 0.1 mg SPA bead coated with wheat-germ aglutinin (WGA-PVT-Polyethylene Imine beads from Amersham) and 0.2 nM of the radiolabelled [$^{125}$I]-OVTA (OVTA being Ornithin Vasoactive, an analogue of OT for competitive binding experiments). Non-specific binding was determined in the presence of 1 μM Oxytocin. The total assay volume was 100 μl. The plates (Corning® NBS plate) were incubated at room temperature for 30 min and counted on a Mibrobeta® plate scintillation counter. Competitive binding was performed in presence of compounds of formula (I) at the following concentrations: 30 μM, 10 μM, 1 μM, 300 nM, 100 nM, 10 nM, 1 nM, 100 pM, 10 pM. The competitive binding data were analysed using the iterative, nonlinear, curve-fitting program, "Prism" (GraphPad Software, Inc).

The ability of pyrrolidine derivatives of formula (I) to inhibit the binding of $^{125}$I-OVTA to the OT-receptor was assessed using the above described in vitro biological assay. Representative values for some example compounds are given in Table I where the binding affinity of test compounds from the above examples is expressed by the inhibition constant (Ki; nM). From these values, it can be derived that said test compounds according to formula (I) do show a significant binding to the oxytocin receptor.

TABLE I

| Example No. | IUPAC-Name | Binding Affinity hOT-R (Ki [nM]) |
|---|---|---|
| 1 | methyl [(2S)-1-(biphenyl-4-ylcarbonyl)-4-(methoxyimino)pyrrolidin-2-yl]acetate | 37 |
| 2 | methyl 3-[(2R,4EZ)-1-(biphenyl-4-ylcarbonyl)-4-(methoxyimino)pyrrolidin-2-yl]propanoate | 144 |
| 3 | cyclopentyl [(2S,4EZ)-1-(biphenyl-4-ylcarbonyl)-4-(methoxyimino)pyrrolidin-2-yl]acetate | 46 |
| 5 | 2-[(2S,4EZ)-1-(biphenyl-4-ylcarbonyl)-4-(methoxyimino)pyrrolidin-2-yl]-N-[(2S)-2-hydroxy-2-phenylethyl]acetamide | 67 |
| 6 | 3-[(2R,4EZ)-1-(biphenyl-4-ylcarbonyl)-4-(methoxyimino)pyrrolidin-2-yl]-N-[(2S)-2-hydroxy-2-phenylethyl]propanamide | 77 |
| 9 | (3EZ,5S)-1-(biphenyl-4-ylcarbonyl)-5-(2-morpholin-4-yl-2-oxoethyl)pyrrolidin-3-one O-methyloxime | 142 | b) Functional Assay No. 1: Inhibition of Oxytocin Mediated $Ca^{2+}$-mobilization by FLIPR® Fluorimetric Imaging Plate Reader)

The action of the OT-receptor triggers a complex cascade of events in the cell that leads to an increase in the intra-cytoplasmic $Ca^{2+}$ concentration. This increase in $Ca^{2+}$ concentration results from both calcium release from the sarcoplasmic reticulum (calcium stores) into cytoplasm and from calcium influx from the extracellular space through $Ca^{2+}$ channels. The $Ca^{2+}$ mobilization into the cytoplasm triggers the contractile machinery of the myometrial cells that leads to uterine contractions (1 and 3).

This assay allows the measurement of the inhibition of OT/OT-R mediated calcium mobilization by test compounds of formula (I).

FLIPR® is a fluorimetric imaging device using a laser (Argon-ion laser) for simultaneous illumination and reading (cooled CCD camera) of each well of a 96-well-plate, thus enabling rapid measurements on a large number of samples.

Preparing the plates: FLIPR-plates were pre-coated with PLL (Poly-L-Lysine) 10 µg/ml+0.1% gelatine to attach HEK293EBNA cells Human Embryonic Kidney cells expressing the hOT receptor) and incubated for 30 min up to 2 days at 37° C. The cells were plated out into 96-well-plates (60000 cells/well).

Labelling with fluo-4: 50 µg of fluo-4 (Ca2+sensitive fluorescent dye) were dissolved in 20 µl pluronic acid (20% in DMSO). The dissolved fluo-4 was then diluted in 10 ml DMEM (Dubecco's Minimal Essential Medium)-F12 culture medium. The plates were washed one time with DMEM-F12 medium. 100 µl of the fluo-4 containing-DMEM-F12 medium were added to the HEK-cells that were incubated for 1.5-2 h in this fluorescent medium. Fluo-4 is taken up by the cytoplasm of the cells.

Buffer: 145 mM NaCl, 5 mM KCl, 1 mM $MgCl_2$, 10 mM Hepes, 10 mM Glucose, EGTA (Ethylene-bis oxyethylene nitrilo tetraacetic acid). The pH was adjusted to 7.4.

Performance of the assay, A minimum of 80 µl/well of compounds of formula (I) (5×) in the above buffer (1×) was prepared (96-well-plates). The compounds of formula (I) were added to the 96-well-plates at different concentrations (30 µM, 10 µM, 1 82 M, 300 nM, 100 nM, 10 nM, 1 nM, 100 pM, 10 pM). OT was added at a concentration of 40 nM.

The relative fluorescence of Fluo-4 ($\lambda_{ex}$=488 nm, $\lambda_{em}$=590 nm) is then measured by the FLIPR in presence or absence of compounds of formula (I). The fluorescence of the marker being sensitive to the amount of $Ca^{2+}$, the $Ca^{2+}$ movements can be detected. Then, it can be determined the ability of compounds of formula (I) to antagonize the oxytocin-induced intracellular $Ca^{2+}$-mobilization mediated by the oxytocin receptor.

c) Functional Assay No.2 Inhibition of IP3 (Inositol Tri-Phosphate)-Synthesis in HEK/EBNA-OTR Cells The interaction of OT on the OT-receptor leads to the IP3 synthesis, second messenger for $Ca^{2+}$ release from sarcoplasmic reticulum involved in the uterine contraction triggering process (3).

This assay can be used to show the inhibition of the OT/OT-R mediated IP3 synthesis by using test compounds of formula (I).

Stimulation of the cells: HEK/EBNA OTR (rat or human) cells are plated out into costar 12-well plates, and equilibrated for 15-24 h with 4 µCi/ml radiolabelled [$^3$H]-Inositol with 1% FCS (0.5 ml/well) and without inositol supplement. The medium containing the label is aspirated. DMEM medium (without FCS, inositol), 20 mM Hepes (4-(2-hydroxyethyl)-1-piperazine-ethane-sulphonic acid), 1 mg/ml BSA containing 10 mM LiCl (freshly prepared), are added and incubated for 10-15 min at 37° C. The agonist (i.e. oxytocin used at a concentration of 10 nM) and the antagonists (i.e. the tests compounds of formula (I) can be used in a concentration of 10 µM, 1 µM, 300 nM, 100 nM, 10 nM, 1 nM, 100 pM, 10 pM, 3 pM) can be added at the required time (15-45 min), followed by aspiration of the medium. In the presence of OT, the radiolabelled inositol is converted to radiolabelled IP3. Antagonizing OT at the OT-receptor inhibits the IP3 formation.

The amount of the radiolabelled IP3 may be determined through the ensuing work-up. The reaction is stopped with 1 ml STOP-solution (i.e. 0.4 M perchloric acid), and let sit for 5-10 min at Room Temperature. Then, 0.8 ml are transferred into tubes containing 0.4 ml of neutralizing solution (0.72 M KOH/0.6M $KHCO_3$), and the tubes vortexed and kept in the cold at least for 2 h.

Separation of IP's: The samples are spun in a table top centrifuge at 3000-4000 rpm for 15 min. 1 ml of the supernatant is transferred to new tubes containing 2.5 ml $H_2O$. Packed resin (Dowex AG1X8) is equilibrated with 20 ml $H_2O$, and the whole samples are poured onto the chromatography columns, thus separating the mixture. To remove free inositol, two washes with 10 ml $H_2O$ are carried out.

Elution of total IP's: Elution is achieved using 3 ml 1M ammonium formate/0.1M formic acid. The eluant is collected in scintillation counting tubes, after the addition of 7 ml of scintillation liquid. The amount of [$^3$H]-IP3 is determined by a scintillating counter.

The ability of compounds of formula (I) to effectively antagonize oxytocin-induced IP3-synthesis mediated by the oxytocin receptor, can be assessed using the above described in vitro biological assay.

d) In Vivo Model for Inhibition of Uterine Contractions

The assay evaluates the biological effect of tested compounds in an in vivo model of preterm labor, premature birth.

Non-pregnant Charles River CD (SD) BR female rats (9-10 weeks old, 200-250 g) were treated at 18 and 24 hours before the experiment with 250 µg/kg, i.p. diethylstilbestrol (DES). For the assay, the animal was anaesthetised with urethane (1.75 g/kg, i.p.) and placed on a homeothermic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P23ID Gould Statham pressure transducer.

One jugular vein was isolated, cannulated with a PE60 tubing and connected to a butterfly needle to provide an i.v. route of administration of the test compounds via a dispensing syringe.

In the case of intraduodenal administration of the test compounds, the duodenum can be isolated and similarly cannulated through a small incision in its wall.

One carotid artery was also isolated and cannulated with PE60 catheter and connected to a suitable syringe for blood sample collection.

After a stabilization period and throughout the experiment, the same dose of oxytocin was repeatedly injected intravenously at 30-min intervals. When reproducible contractile responses of the uterus to the same OT stimulus (selected dose of oxytocin) were obtained, the dose of the test or of the reference (vehicle) was administered. Further injection cycles of the same dose of oxytocin, were continued (OT injections at 30-min intervals) for a suitable time after treatment to assess the inhibitory effects and the reversibility of these effects.

The contractile response of the uterus to oxytocin was quantified by measuring the intra-uterine pressure and the number of contractions. The effect of the reference and test compounds was evaluated by comparing pre- and post-treatment pressure values. In addition, contractions of the uterine were measured at 5, 40, 75, 110, 145 and 180 minutes after test compound administration.

The activities of the pyrrolidine derivatives claimed in the Formula (I) can be assessed using the above described in vivo biological assay.

REFERENCES

1. Gimpl G. and Fahrenholz, F. *Physiological Reviews* 2001, 81, 629-683
2. Maggi, M. et al. *J. Clin. Endocrinol. Metabol.* 1990, 70, 1142-1154.
3. Mitchell, B. F. and Schmid, B. J. *Soc. Gynecol. Invest.* 2001, 8,122-33.
4. Thorton, S. et al., *Experimental Physiology* 2001; 86, 297-302.
5. Evans B. E. et al. *J.Med.Chem.* 1992, 35, 3919-3927.
6. Gennaro, A. R. et al., *Remington's Pharmaceutical Sciences*, 20th Edition, 2000, Marck Publishing Company, Easton, Pa.
7. T. W. Greene et al. John Wiley & Sons Inc, Third Edition 1999.
8. R. C. Larock, Wiley VCH 1999.
9. E. Breitmaier, W. Voelter Carbon-13 NMR Spectroscopy, 3rd Ed, p. 240, VCH, 1987.
10. Philip J. Kocienski, in "*Protecting Groups*" Georg Thieme Verlag Stuttgart, New York, 1994.
11. Cook, N. D. et al. *Pharmaceutical Manufacturing International* 1992; p. 49-53
12. WO 01/72705 (Applied Research Systems ARS Holding)
13. WO 02/074741 (Applied Research Systems ARS Holding)
14. WO 02/102799 (Applied Research Systems ARS Holding)

The invention claimed is:

1. A pyrrolidine derivative of Formula I:

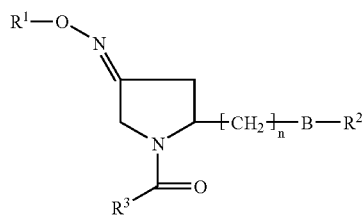

(I)

its optically active forms as enantiomers, diastereomers, mixtures of these and its racemate forms, as well as salts thereof, wherein:

$R^1$ is selected from the group consisting of H and $C_1$-$C_6$-alkyl;

B is selected from the group consisting of —COO, —CONR$^4$, oxadiazole, thiadiazole or benzimidazole;

$R^2$ is selected from the group consisting of hydrogen, $C_1$-$C_6$-alkyl, aryl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_2$-$C_6$-alkynyl, $C_2$-$C_6$-alkynyl aryl, $C_2$-$C_6$-alkynyl heteroaryl, $C_3$-$C_8$-cycloalkyl, heterocycloalkyl, $C_1$-$C_6$-alkyl cycloalkyl, $C_1$-$C_6$-alkyl heterocycloalkyl, $C_1$-$C_6$-alkyl carboxy, acyl, $C_1$-$C_6$-alkyl acyl, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, $C_1$-$C_6$-alkyl acylamino, $C_1$-$C_6$-alkyl ureido, amino, $C_1$-$C_6$-alkyl amino, sulfonyloxy, $C_1$-$C_6$-alkyl sulfonyloxy, sulfonyl, $C_1$-$C_6$-alkyl sulfonyl, sulfinyl, $C_1$-$C_6$-alkyl sulfinyl, $C_1$-$C_6$-alkyl sulfanyl, and $C_1$-$C_6$-alkyl sulfonylamino;

$R^3$ is selected from the group consisting of aryl and heteroaryl;

$R^4$ is selected from the group consisting of H, $C_1$-$C_6$-alkyl, $C_1$-$C_6$-alkyl aryl, $C_1$-$C_6$-alkyl heteroaryl, aryl, and heteroaryl; or $R^2$ and $R^4$ can form together with the N atom to which they are linked to, a 5-8 membered saturated or unsaturated heterocycloalkyl ring; and n is an integer from 1 to 3.

2. A pyrrolidine derivative according to claim 1, wherein $R^1$ is methyl.

3. A pyrrolidine derivative according to claim 1, wherein $R^3$ is a biphenyl.

4. A pyrrolidine derivative according to claim 1, wherein n is an integer 1 or 2.

5. A pyrrolidine derivative according to claim 1, wherein B is —COO, CONR$^4$ or an oxadiazole.

6. A pyrrolidine derivative according to claim 1, wherein $R^2$ is selected from the group consisting of H, $C_1$-$C_6$ alkyl, and 3-8 membered cycloalkyl.

7. A pyrrolidine derivative according to claim 1, wherein $R^2$ and $R^4$ form together with the N atom to which they are linked, a piperidinyl, piperazinyl or morpholino moiety.

8. A pyrrolidine derivative according to claim 1, wherein wherein $R^1$ is methyl, $R^3$ is a biphenyl moiety, B is —COO, CONR$^4$ or a 1,2,4 oxadiazole moiety.

9. A pyrrolidine derivative according to claim 1 selected from the group consisting of:

3-[(2R, 4EZ)-1-(biphenyl-4-ylcarbonyl)-4-(methoxyimino)pyrrolidin-2-yl] propanoic acid, methyl 3-[(2R,4EZ)-1-(biphenyl-4-ylcarbonyl)-4-(methoxyimino)pyrrolidin-2-yl] propanoate, cyclopentyl [(2S,4EZ)-1-(biphenyl-4-ylcarbonyl)-4-(methoxyimino)pyrrolidin-2-yl] acetate, cyclopentyl 3-[(2R,4EZ)-1-(biphenyl-4-ylcarbonyl)-4-(methoxyimino)pyrrolidin-2-yl] propanoate, 2-[(2S,4EZ)-1-(biphenyl-4-ylcarbonyl)-4-(methoxyimino)pyrrolidin-2-yl]-N-[(2S)-2-hydroxy-2-phenylethyl] acetamide, 3-[(2R,4EZ)-1-(biphenyl-4-ylcarbonyl)-4-(methoxyimino)pyrrolidin-2-yl]-N-[(2S)-2-hydroxy-2-phenylethyl] propanamide, 2-[(2S,4EZ)-1-(biphenyl-4-ylcarbonyl)-4-(methoxyimino)pyrrolidin-2-yl] acetamide, 3-[(2R,4EZ)-1-(biphenyl-4-ylcarbonyl)-4-(methoxyimino)pyrrolidin-2-yl] propanamide, (3EZ,5S)-1-(biphenyl-4-ylcarbonyl)-5-(2-morpholin-4-yl-2-oxoethyl)pyrrolidin-3-one O-methyloxime, (3EZ,5R)-1-(biphenyl-4-ylcarbonyl)-5-(3-morpholin-4-yl-3-oxopropyl)pyrrolidin-3-one O-methyloxime, N-(2-aminophenyl)-2-[(2S,4EZ)-1-(biphenyl-4-ylcarbonyl)-4-(methoxyimino) pyrrolidin-2-yl] acetamide, N-(2-aminophenyl)-3-[(2R,4EZ)-1-(biphenyl-4-ylcarbonyl)-4-(methoxyimino) pyrrolidin-2-yl] propanamide, (3EZ,5S)-5-(1H-benzimidazol-2-ylmethyl)-1-(biphenyl-4-ylcarbonyl)pyrrolidin-3-one O-methyloxime.

(3EZ,5R)-5-[2-(1H-benzimidazol-2-yl)ethyl]-1-(biphenyl-4-ylcarbonyl)pyrrolidin-3-one O-methyloxime, (3EZ,5S)-1-(biphenyl-4-ylcarbonyl)-5-[(3-methyl-1,2,4-oxadiazol-5-yl)methyl] pyrrolidin-3-one O-methyloxime, (3EZ,5R)-1-(biphenyl-4-ylcarbonyl)-5-[2-(3-methyl-1,2,4-oxadiazol-5-yl)ethyl] pyrrolidin-3-one O-methyloxime, (3EZ,5S)-1-(biphenyl-4-ylcarbonyl)-5-{[3-(2-hydroxyethyl)-1,2,4-oxadiazol-5-yl] methyl}pyrrolidin-3-one O-methyloxime, and (3EZ,5R)-1-(biphenyl-4-ylcarbonyl)-5-{2-[3-(2-hydroxyethyl)-1,2,4-oxadiazol-5-yl] ethyl}pyrrolidin-3-one O-methyloxime.

10. A medicament comprising a pyrrolidine according to claim 1.

11. A method of treating preterm labor, premature birth or dysmenorrheal in a patient in need thereof comprising administering an effective dose of a medicament comprising a pyrrolidine according to claim 1 as well as optically active forms as enantiomers, diastereomers and mixtures of the same.

12. A pharmaceutical composition containing a pyrrolidine derivative according to claim 1 and a pharmaceutically acceptable carrier, diluent or excipient thereof.

13. A method of preparing a pyrrolidine derivative according to claim 1 comprising reacting a carboxylic acid (II) with an alcohol (III)

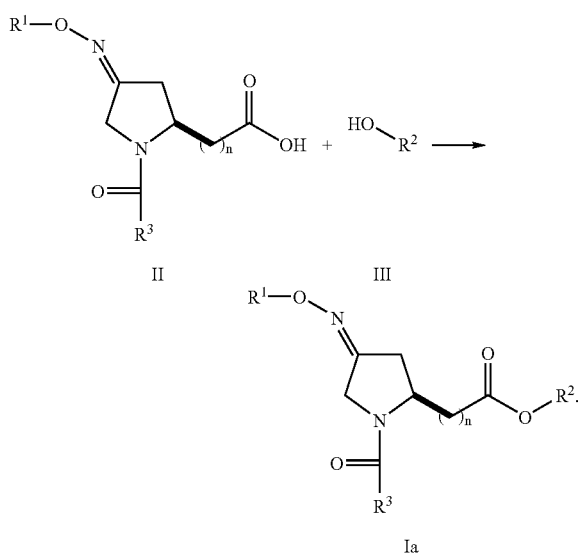

14. A method of preparing a pyrrolidine derivative according to claim 1 comprising reacting the carboxylic acid (II) with an amine (XIII)

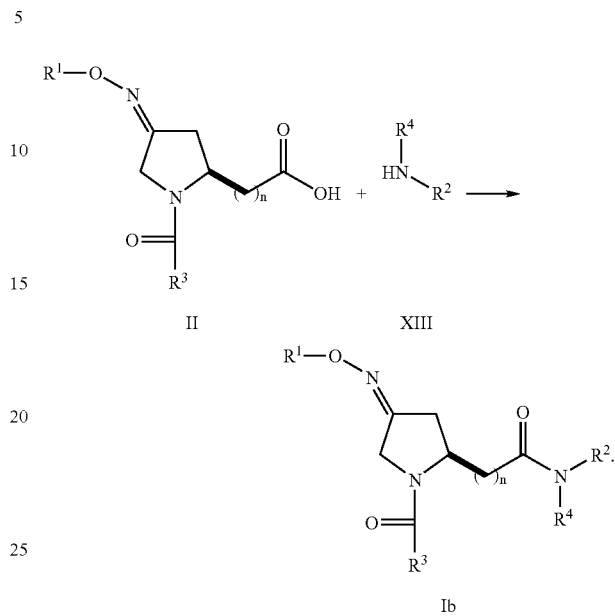

15. A method of preparing a pyrrolidine derivative according to claim 1 comprising reacting the carboxylic acid (II) with an amidoxime (XIV)

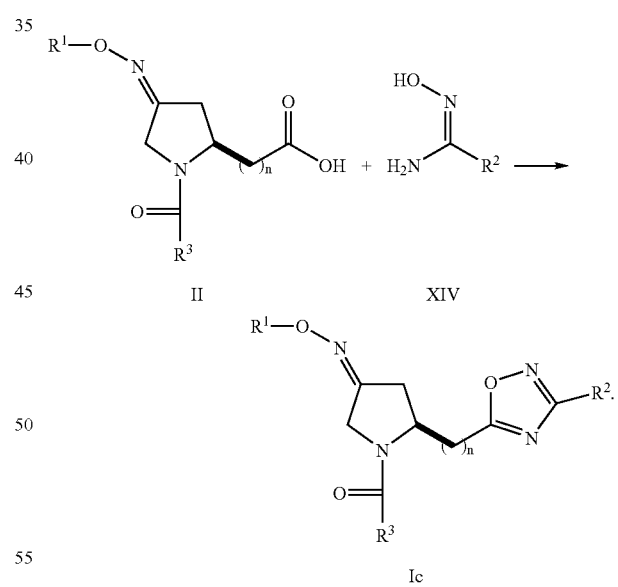

* * * * *